United States Patent [19]

Van Daele et al.

[11] Patent Number: 5,041,454

[45] Date of Patent: Aug. 20, 1991

[54] NOVEL SUBSTITUTED N-(1-ALKYL-3-HYDROXY-4-PIPERIDINYL)-BENZAMIDES

[75] Inventors: Georges H. P. Van Daele, Turnhout; Freddy F. Vlaeminck, Lille; Michel A. J. De Cleyn, Merksplas, all of Belgium

[73] Assignee: Janssen Pharmaceutica N.V., Beerse, Belgium

[21] Appl. No.: 511,117

[22] Filed: Apr. 19, 1990

Related U.S. Application Data

[60] Division of Ser. No. 239,903, Sep. 2, 1988, Pat. No. 4,975,439, which is a continuation-in-part of Ser. No. 101,115, Sep. 25, 1987, abandoned.

[51] Int. Cl.$^5$ .................. A61K 31/38; A61K 31/445; C07D 211/22; C07D 28/02; C07D 267/02

[52] U.S. Cl. .................................. 514/316; 514/211; 514/212; 514/218; 514/227.8; 514/235.5; 514/252; 514/256; 514/274; 514/278; 514/318; 514/326; 514/327; 514/224.2; 514/230.5; 514/249; 540/524; 540/544; 540/553; 540/597; 544/58.4; 544/130; 544/310; 544/316; 544/360; 544/52; 544/105; 544/355; 546/15; 546/188; 546/194; 546/208; 546/209; 546/210; 546/221

[58] Field of Search ................. 546/209, 210, 15, 188, 546/194, 208; 544/58.4, 130, 52, 310, 316, 355, 360, 105; 540/524, 544, 553, 597; 514/212, 218, 227.8, 235.5, 252, 256, 274, 278, 316, 318, 326, 230.5, 224.2, 249

[56] References Cited

FOREIGN PATENT DOCUMENTS 0076530 4/1983 European Pat. Off. .
0145037 6/1985 European Pat. Off. .
0251417 1/1988 European Pat. Off. .

Primary Examiner—Johann Richter
Attorney, Agent, or Firm—Charles J. Metz

[57] ABSTRACT

Substituted N-(1-alkyl-3-hydroxy-4-piperidinyl)benzamides, their N-oxide forms, their pharmaceutically acceptable acid addition salts and stereochemically isomeric forms having gastrointestinal motility stimulating properties, compositions containing the same, and methods of treating warm-blooded animals suffering from motility disorders of the gastrointestinal system.

25 Claims, No Drawings

NOVEL SUBSTITUTED N-(1-ALKYL-3-HYDROXY-4-PIPERIDINYL)BENZAMIDES

CROSS REFERENCE TO RELATED APPLICATIONS

This is a division of Ser. No. 07/239,903 filed on 9/2/88, now U.S. Pat. No. 4,975,439, which is a continuation-in-part of Ser. No. 07/101,115 filed on 9/25/87, now abandoned.

BACKGROUND OF THE INVENTION

In the European Patent No. 76.530 which corresponds to the U.S. Ser. No. 403,603 there are described N-(1-alkyl-3-hydroxy-4-piperidinyl)benzamide derivatives which compounds are useful as stimulators of the motility of gastrointestinal system.

The compounds of the present invention differ therefrom by the fact that the piperidinyl moiety is substituted in a previously undisclosed manner and by their favorable gastrointestinal motility stimulating properties and particularly their improved capability to accelerate gastric emptying.

DESCRIPTION OF THE INVENTION

The present invention is concerned with novel N-(4-piperidinyl)benzamides having the formula

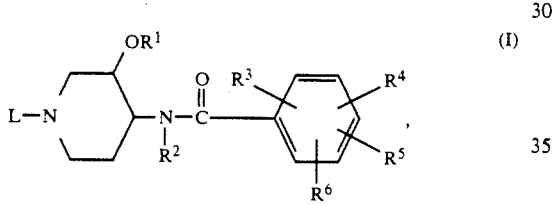

the N-oxide forms, the pharmaceutically acceptable acid addition salts and stereochemically isomeric forms thereof, wherein $R^1$ is hydrogen, $C_{1-6}$alkyl, aryl$C_{1-6}$alkyl, $C_{1-6}$alkylcarbonyl, $C_{1-6}$alkyloxycarbonyl, aryloxycarbonyl, amino$C_{1-6}$alkyl, mono- or di($C_{1-6}$alkyl)amino$C_{1-6}$alkyl, aminocarbonyl, mono- or di($C_{1-6}$alkyl)aminocarbonyl, pyrrolidinylcarbonyl or piperidinylcarbonyl;

$R^2$ is hydrogen or $C_{1-6}$alkyl;

$R^3$, $R^4$ and $R^5$ each independently are hydrogen, $C_{1-6}$alkyl, $C_{1-6}$alkyloxy, halo, hydroxy, cyano, nitro, amino, trifluoromethyl, mono- or di($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylaminosulfonyl, $C_{1-6}$alkylsulfinyl, $C_{1-6}$alkylsulfonyl, $C_{1-6}$alkylthio, mercapto, aryl$C_{1-6}$alkyloxy or aryloxy;

$R^6$ is hydrogen, hydroxy, $C_{1-6}$alkyl, $C_{1-6}$alkyloxy, halo or amino;

L is a radical of formula

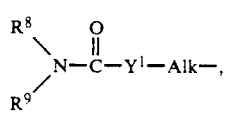

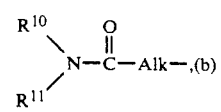

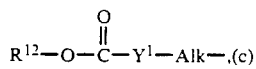

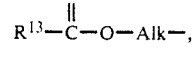

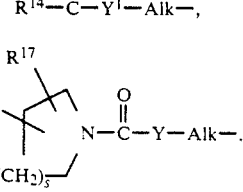

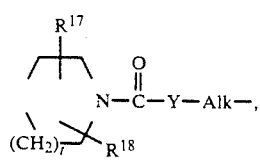

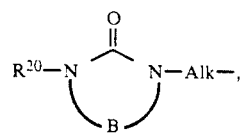

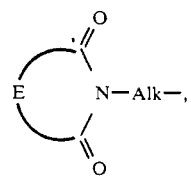

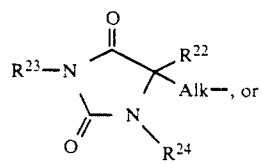

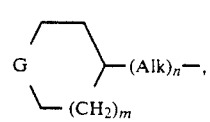

wherein

Alk is $C_{1-6}$alkanediyl or $C_{3-6}$alkenediyl;

$Y^1$ is O, S or $NR^7$; whereas Y is O, S, $NR^7$ or a direct bond; said $R^7$ being hydrogen or $C_{1-6}$alkyl;

$R^8$ and $R^9$ each independently are hydrogen, $C_{1-6}$alkyl, $C_{1-6}$alkyloxy, aryl, $C_{3-6}$cycloalkyl, aryl$C_{1-6}$alkyl or ($C_{3-6}$cycloalkyl)$C_{1-6}$alkyl; provided that $R^8$ and $R^9$ are other than hydrogen when $R^7$ is hydrogen;

$R^{10}$ is $C_{1-6}$alkyl, $C_{3-6}$cycloalkyl, aryl$C_{1-6}$alkyl, $C_{1-6}$alkyloxy or ($C_{3-6}$cycloalkyl)$C_{1-6}$alkyl;

$R^{11}$ is aryl, aryl$C_{1-6}$alkyl, $C_{1-6}$alkyloxy or ($C_{3-6}$cycloalkyl)$C_{1-6}$alkyl;

$R^{12}$ is $C_{1-6}$alkyl, aryl or aryl$C_{1-6}$alkyl;

$R^{13}$ is $C_{1-6}$alkyl, $C_{3-6}$cycloalkyl, aryl, aryl$C_{1-6}$alkyl or ($C_{3-6}$cycloalkyl)$C_{1-6}$alkyl;

$R^{14}$ is aryl$C_{1-6}$alkyl wherein the $C_{1-6}$alkyl moiety is substituted with hydroxy or $C_{1-6}$alkylcarbonyloxy;

$R^{15}$ and $R^{16}$ each independently are hydrogen, $C_{1-6}$alkyl, hydroxy, $C_{1-6}$alkyloxy, amino, mono- or di($C_{1-6}$alkyl)amino, hydroxyC$_{1-6}$alkyl, C$_{1-6}$alkylcarbonyl, C$_{1-6}$alkyloxycarbonyl, aminocarbonyl, mono- or di(C$_{1-6}$alkyl)aminocarbonyl or 2-C$_{1-6}$alkyl-1,3-dioxolan-2-yl; or R$^{15}$ and R$^{16}$ combined with the carbon atom bearing said R$^{15}$ and R$^{16}$ may form a carbonyl or a 1,3-dioxolan-2ylidene radical;

s is the integer 1,2 or 3;

A is O, S or NR$^{19}$; said R$^{19}$ being hydrogen, C$_{1-6}$alkyl, aryl, pyridinyl, pyrimidinyl, C$_{1-6}$alkylcarbonyl, C$_{1-6}$alkyloxycarbonyl or arylC$_{1-6}$alkyl;

R$^{17}$ and R$^{18}$ each independently are hydrogen or C$_{1-6}$alkyl, or when A is NR$^{19}$ R$^{17}$ and R$^{18}$ taken together may form a fused benzene residue being optionally substituted with halo or C$_{1-6}$alkyl;

t is the integer 1 or 2;

R$^{20}$ is hydrogen or C$_{1-6}$alkyl;

B is a bivalent radical of formula —CH$_2$—CH$_2$—, —C(=O)—CH$_2$— or —CH$_2$—CH$_2$—CH$_2$—, wherein each hydrogen atom independently may be replaced by C$_{1-6}$alkyl substituents, or when R$^{20}$ is C$_{1-6}$alkyl said bivalent radical may also be 1,2-benzenediyl optionally substituted with halo or C$_{1-6}$alkyl;

E is a bivalent radical of formula —CH$_2$—CH$_2$—, —CH$_2$—N(R$^{21}$)— or —CH$_2$—CH$_2$—CH$_2$—, wherein each hydrogen atom independently may be replaced by C$_{1-6}$alkyl, or said bivalent radical may also be 1,2-benzenediyl optionally substituted with halo or C$_1$alkyl; said R$^{21}$ being hydrogen or C$_{1-6}$alkyl;

R$^{22}$, R$^{23}$ and R$^{24}$ each independently are hydrogen or C$_{1-6}$alkyl;

n and m are both independently 0 or 1;

G is carbonyl, carboxymethylene, C$_{1-6}$alkyloxycarbonylmethylene, C$_{1-6}$alkylcarbonylmethylene, 5,5-dimethyl-1,3-dioxan-2-ylidene or 1,3-dioxolan-2-ylidene; and aryl is phenyl optionally substituted with 1, 2 or 3 substituents each independently selected from halo, hydroxy, C$_{1-6}$alkyl, C$_{1-6}$alkyloxy, aminosulfonyl, C$_{1-6}$alkylcarbonyl, nitro, trifluoromethyl, amino, aminocarbonyl and phenylcarbonyl.

As used in the foregoing definitions the term halo is generic to fluoro, chloro, bromo and iodo; the term C$_{1-6}$alkyl is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; the term C$_{3-6}$cycloalkyl is generic to cyclopropyl, cyclobutyl, cyclopentyl and cyclohexyl; the term C$_{1-6}$alkanediyl is meant to include bivalent straight or branch chained alkanediyl radicals having from 1 to 6 carbon atoms such as, for example, methylene, 1,2-ethanediyl, 1,3-propanediyl, 1,4-butanediyl, 1,5-pentanediyl, hexanediyl and the branched isomers thereof; the term C$_{3-6}$alkenediyl is meant to include bivalent straight or branch chained alkenediyl radicals having from 3 to 6 carbon atoms.

Said N-oxides of the compounds of formula (I) are meant to comprise those compounds of formula (I) wherein one or several nitrogen atoms are oxidated to the so called N-oxide, particularly those N-oxides wherein the piperidine-nitrogen is N-oxidated.

Said acid addition salts as mentioned hereinbefore are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, 2,3-dihydroxybutanedioic, 2-hydroxy-1,2,3-propanetricarboxylic, methanesulfonic, ethansulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term acid addition salt also comprises the hydrates and solvent addition forms which the compounds of formula (I) are able to form. Examples of such forms are e.g. hydrates, alcoholates and the like. Said solvates are meant to be included within the scope of the present invention.

The compounds of formula (I) have at least two asymmetric carbon atoms in their structure, namely those located in the 3- and the 4-position of the piperidine nucleus, and consequently, the substituents in the said 3- and 4-positions of the piperidine nucleus have either a trans or a cis configuration. (S. Cahn, C. Ingold and V. Prelog in Angew. Chem., Int. Ed. Engl., 5, 385–511 (1966).

Preferred compounds within the invention are those compounds of formula (I) wherein R$^1$ is hydrogen, C$_{1-6}$alkyl, aryloxycarbonyl, mono- or di-(C$_{1-6}$alkyl)aminocarbonyl, pyrrolidinylcarbonyl or piperidinylcarbonyl; and/or R$^2$ is hydrogen; and/or R$^3$, R$^4$ and R$^5$ each independently are hydrogen, halo, C$_{1-6}$alkyloxy, amino, mono- or di(C$_{1-6}$alkyl)amino, C$_{1-6}$alkylcarbonylamino, nitro, aminosulfonyl, C$_{1-6}$-alkylaminosulfonyl or C$_{1-6}$alkylsulfonyl.

Particularly preferred compounds within the invention are those preferred compounds of formula (I) wherein the substituents on the 3- and the 4-position of the piperidine ring have the cis configuration.

More particularly preferred compounds within the invention are those compounds of formula (I) wherein aryl is phenyl optionally substituted with 1, 2 or 3 substituents each independently selected from halo, hydroxy, C$_{1-4}$ alkyl and C$_{1-4}$alkyloxy; Alk is a C$_{1-4}$-alkanediyl radical; and L is a radical of formula (a) wherein Y$^1$ is NR$^7$, said R$^7$ being hydrogen or C$_{1-4}$alkyl, and R$^8$ and R$^9$ are both C$_{1-4}$alkyl; or (b) wherein R$^{10}$ is C$_{1-4}$alkyl and R$^{11}$ is aryl or C$_{1-4}$alkyloxy; or (c) wherein Y$^1$ is NR$^7$, said R$^7$ being hydrogen or C$_{1-4}$-alkyl and R$^{12}$ is C$_{1-4}$alkyl; or (d) wherein R$^{13}$ is C$_{1-4}$alkyl, C$_{3-6}$cycloalkyl or aryl; or (e) wherein Y$^1$ is NR$^7$, said R$^7$ being hydrogen or C$_{1-4}$alkyl; or (f) wherein Y is O, NR$^7$ or a direct bond, R$^{15}$ is hydrogen, C$_{1-4}$alkyl, hydroxy, C$_{1-4}$alkyloxy, amino, mono- or di(C$_{1-4}$-alkyl)amino, hydroxyC$_{1-4}$-alkyl, C$_{1-4}$alkylcarbonyl, C$_{1-4}$-alkyloxycarbonyl or aminocarbonyl and R$^{16}$ is hydrogen or C$_{1-4}$alkyl, or R$^{15}$ and R$^{16}$ combined with the carbon atom bearing said R$^{15}$ and R$^{16}$ may form a carbonyl or a 1,3-dioxolan-2-ylidene radical; or (g) wherein Y is O, NR$^7$ or a direct bond and A is O or NR$^{19}$, said R$^{19}$ being hydrogen, C$_{1-6}$alkyl, aryl pyridinyl, pyrimidinyl, C$_{1-4}$alkylcarbonyl, C$_{1-4}$alkyloxycarbonyl or arylC$_{1-4}$alkyl; or (h) wherein B is 1,2-ethanediyl or when R$^{20}$ is C$_{1-4}$alkyl B may also be 1,2-benzenediyl optionally substituted with halo or C$_{1-4}$alkyl; or (i) wherein E is 1,3-propanediyl optionally substituted with $C_{1-4}$alkyl, 1,2-benzenediyl optionally substituted with halo or $C_{1-4}$alkyl, or a bivalent radical of formula —$CH_2$—$N(R^{21})$—, said $R^{21}$ being hydrogen or $C_{1-4}$alkyl; or (j) wherein $R^{23}$ and $R^{24}$ are both hydrogen; or L is a radical of formula (k) wherein G is carbonyl, $C_{1-4}$alkoxycarbonylmethylene, $C_{1-6}$alkylcarbonylmethylene, 5,5-dimethyl-1,3-dioxan-2-ylidene or 1,3-dioxolan-2-ylidene.

Still more particularly preferred compounds within the invention are those more particularly preferred compounds of formula (I) wherein the benzamide part is substituted on the meta position with $R^3$ being chloro, bromo, $C_{1-4}$alkylaminosulfonyl, aminosulfonyl or $C_{1-4}$alkylsulfonyl, on the para position with $R^4$ being amino and on the ortho position with $R^5$ being hydroxy or $C_{1-4}$alkyloxy.

Especially preferred compounds within the invention are those more particularly preferred compounds of formula (I) wherein $R^1$ is hydrogen or methyl and $R^3$, $R^4$ and $R^5$ respectively are 2-methoxy, 4-amino and 5-chloro.

An interesting subgroup of compounds of formula (I) comprises those compounds, preferred, particularly preferred, more particularly preferred and especially preferred compounds wherein L is a radical of formula (a), (d) or (e).

Another interesting subgroup of compounds of formula (I) comprises those compounds, preferred, particularly preferred, more particularly preferred and especially preferred compounds wherein L is a radical of formula (k).

Still another interesting subgroup of compounds of formula (I) comprises those compounds, preferred, particularly preferred, more particularly preferred and especially preferred compounds wherein L is a radical of formula (f), (g), (h) or (i).

In order to simplify the structural representations of the compounds of formula (I) and of certain starting materials and intermediates thereof, the radical

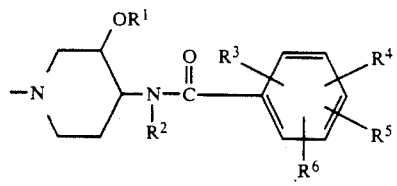

will hereafter be represented by the symbol D.

The compounds of formula (I) can be prepared by N-alkylating a piperidine of formula (II) with an intermediate of formula (III).

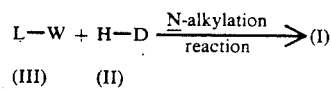

W as used in the reaction of (III) with (II) and in the following reaction scheme is an appropriate leaving group such as, for example, halo, preferably, chloro, bromo or iodo, or a sulfonyloxy group, e.g. methanesulfonyloxy, 4-methylbenzenesulfonyloxy and the like leaving groups.

The N-alkylation reaction of (II) with (III) is conveniently conducted in a reaction-inert solvent such as, for example, an aromatic hydrocarbon, e.g. benzene, methylbenzene, dimethylbenzene and the like; an alkanol, e.g. methanol, ethanol, 1-butanol and the like; a ketone, e.g. 2-propanone, 4-methyl-2-pentanone and the like; an ether, e.g. 1,4-dioxane, 1,1'-oxybisethane, tetrahydrofuran and the like; a polar aprotic solvent, e.g. N,N-dimethylformamide, N,N-dimethylacetamide, dimethyl sulfoxide, hexamethylphosphor triamide, 1,3-dimethyl-3,4,5,6-tetrahydro-2(1H)pyrimidinone, 1,3-dimethyl-2-imidazolidinone, nitrobenzene, 1-methyl-2-pyrrolidnone and the like or a mixture of such solvents.

The addition of an appropriate base such as, for example, an alkali or an earth alkaline metal carbonate, hydrogen carbonate, hydroxide, alkoxide or hydride, e.g. sodium carbonate, sodium hydrogen carbonate, potassium carbonate, sodium hydroxide, sodium methoxide, sodium hydride and the like or an organic base such as, for example an amine e.g. N,N-dimethyl-4-pyridinamine, N,N-diethylethamine, N-(1-methylethyl)-2-propanamine, 4-ethylmorpholine and the like may be utilized to pick up the acid which is liberated during the course of the reaction. In some instances the addition of a iodide salt, preferably an alkali metal iodide, is appropriate. Somewhat elevated temperatures may enhance the rate of the reaction.

In this and the following preparations, the reaction products may be isolated from the reaction mixture and, if necessary, further purified according methodologies generally known in the art, such as, for example, extraction, destillation, crystallization, trituration and chromatography.

The compounds of formula (I) can also be prepared by the amidation reaction of an amine of formula

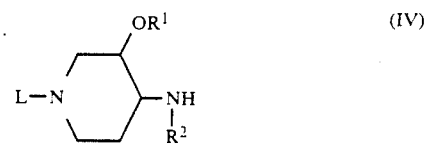

with a carboxylic acid of formula

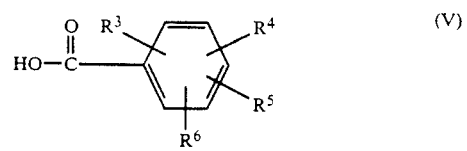

or a functional derivative thereof, such as a halide, a symmetrical or mixed anhydride or an activated ester. Said functional derivative may be generated in situ, or if desired, be isolated and further purified before reacting it with the amine of formula (IV). Functional derivatives may be prepared following art-known procedures, for example, by reacting the carboxylic acid of formula (V) with thionyl chloride, phosphorous trichloride, polyphosphoric acid, phosphoryl chloride and the like, or by reacting the carboxylic acid of formula (V) with an acyl halide, e.g. acetyl chloride, ethyl carbonochloridate and the like. Or the intermediates (IV) and (V) may be coupled in the presence of a suitable reagent capable of forming amides, e.g. dicyclohexylcarbodiimide, 2-chloro-1-methylpyridinium iodide and the like.

Said amidation reactions may conveniently be carried out by stirring the reactants in a suitable reaction-inert solvent, such as, for example, a halogenated hydrocarbon, e.g. dichloromethane, trichloromethane and the like, an aromatic hydrocarbon, e.g. methylbenzene and the like, an ether, e.g. 1,1'-oxybisethane, tetrahydrofuran and the like or a dipolar aprotic solvent, e.g. N,N-dimethylformamide, N,N-dimethylacetamide and the like. The addition of a suitable base may be appropriate, in particular a tertiary amine such as, N,N-diethylethanamine. The water, the alcohol or the acid which is liberated during the course of the reaction may be removed from the reaction mixture according methodologies generally known in the art such as, for example, azeotropical distillation, complexation and salt formation. In some instances it may be advantageous to cool the reaction mixture. Further it may be expedient to protect amino or hydroxy groups during the course of the reaction to avoid unwanted side reactions. Suitable protecting groups comprise readily removeable groups such as, $C_{1-6}$alkylcarbonyl, $C_{1-6}$alkyloxycarbonyl, aryl$C_{1-6}$alkyl and the like protective groups.

The compounds of formula (I) wherein L is a radical of formula (a), (b), (c), (f) or (g), said compounds being represented by formula (I-a-1), can also be prepared by reacting a piperidine of formula (VI) with an alcohol or amine of formula (VII).

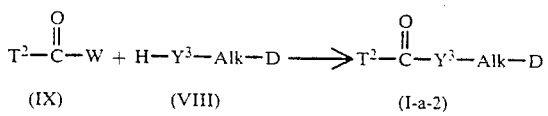

In the reaction of (VII) with (VI) $T^1$- denotes a radical of formula

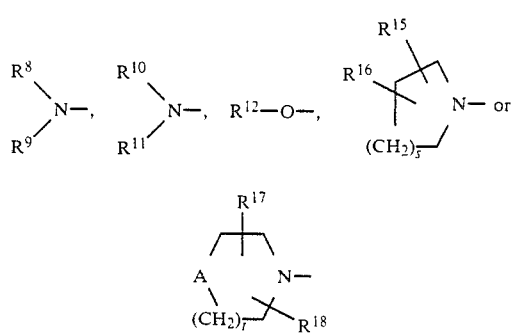

wherein $R^8$, $R^9$, $R^{10}$, $R^{11}$, $R^{12}$, $R^{15}$, $R^{16}$, $R^{17}$, $R^{18}$, s and t have the above described meanings and $Y^2$ denotes O, S, $NR^7$ or a direct bond whichever is allowable under the definition of L.

The compounds of formula (I) wherein L is a radical of formula (a), (c), (d) or (e) and those compounds of formula (I) wherein L is a radical of formula (f) of (g) wherein Y is other than a direct bond, said compounds being represented by (I-a-2), can also be prepared by reacting an alcohol, thiol or amine of formula (VIII) with a reagent of formula (IX).

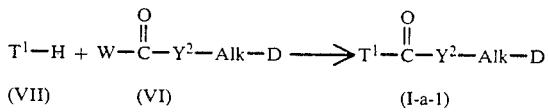

In the reaction of (IX) with (VIII) $T^2$- denotes a radical of formula

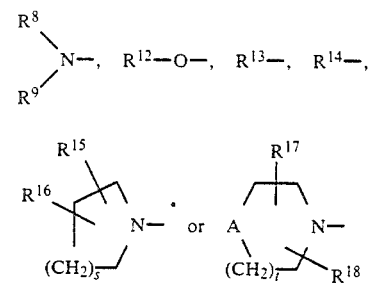

wherein $R^8$, $R^9$, $R^{12}$, $R^{13}$, $R^{14}$, $R^{15}$, $R^{16}$, $R^{17}$, $R^{18}$, s and t have the above described meanings and $Y^3$ denotes O, S or $NR^7$ whichever is allowable under the definition of L.

The reactions of (VII) with (VI) and (VIII) with (IX) are conveniently conducted in a suitable reaction-inert solvent, such as, for example, a hydrocarbon, e.g. benzene, a ketone, e.g., acetone, a halogenated hydrocarbon, e.g. dichloromethane, trichloromethane, an ether, e.g. 1,1'-oxybisethane, tetrahydrofuran and the like. An appropriate base such as, for example, an alkali metal carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (a), (c), (f) or (g), wherein $Y^1$ or Y are NH, said compounds being represented by (I-a-3), can be prepared by reacting an isocyanate of formula (X) with an alcohol or amine of formula (XI).

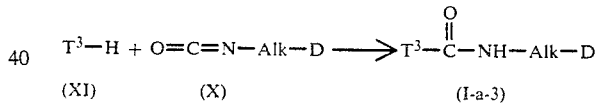

In (I-a-3) and (XI) $T^3$- denotes a radical of formula

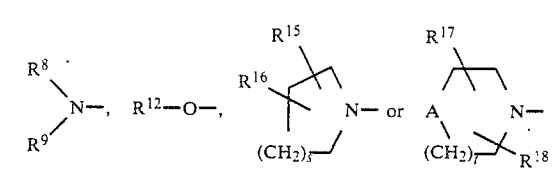

wherein $R^8$, $R^9$, $R^{12}$, $R^{15}$, $R^{16}$, $R^{17}$, $R^{18}$, s and t have the above described meanings.

The compounds of formula (I) wherein L is a radical of formula (a) wherein $R^8$ is hydrogen, said compounds being represented by (I-a-4), can be prepared by reacting an isocyanate of formula (XII) with an alcohol, thiol or amine of formula (VIII).

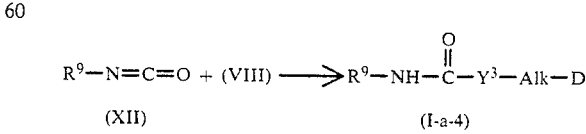

The reaction of (XI) with (X), or (XII) with (VIII) is generally conducted in a suitable reaction-inert solvent such as, for example, an ether, e.g., tetrahydrofuran and the like. Elevated temperatures may be suitable to enhance the rate of the reaction.

The compounds of formula (I) wherein L is a radical of formula (d) or (e), said compounds being represented by formula (I-a-5), may also be prepared by reacting a carboxylic acid of formula (XIII) or a functional derivative thereof with an amine, alcohol or thiol of formula (VIII).

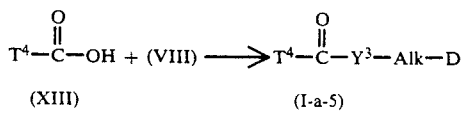

In (I-a-5) and (XIII) $T^4$- denotes a radical of formula $R^{13}$- or $R^{14}$- both having the same meanings as described hereinbefore. The reaction of (XIII) with (VIII) may generally be conducted following art-known esterification- or amidation reaction-procedures. For example, the carboxylic acid may be converted into a reactive derivative, e.g. an anhydride or a carboxylic acid halide, which subsequently, is reacted with (VIII); or by reacting (XIII) and (VIII) with a suitable reagent capable of forming amides or esters, e.g. dicyclohexyl carbodiimide, 2-chloro-1-methylpyridinium iodide and the like. Said reactions are most conveniently conducted in a suitable solvent such as, for example, an ether, e.g. tetrahydrofuran, a halogenated hydrocarbon, e.g. dichloromethane, trichloromethane or a dipolar aprotic solvent, e.g. N,N-dimethylformamide. The addition of a base such as, for example, N,N-diethylethanamide may be appropriate.

The compounds of formula (I) wherein L is a radical of formula (h) or (i), said compounds being represented by formula (I-a-6), can be prepared by N-alkylating an amine of formula (XV) with a piperidine derivative of formula (XIV).

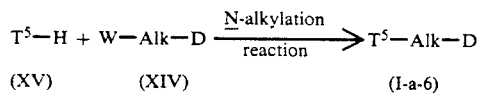

In (I-a-6) and (XV) $T^5$- denotes a radical of formula

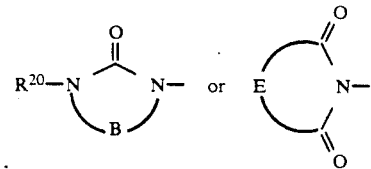

wherein $R^{20}$, B and E have the same meanings as described hereinbefore.

Said N-alkylation reaction is generally carried out following the procedures described hereinabove for the preparation of (I) starting from (II) and (III).

Compounds of formula (I) wherein L is a radical of formula (i), said compounds being represented by formula (I-a-7) may also be prepared by reacting an appropriate anhydride of formula (XVI) with an amine of formula (XVII).

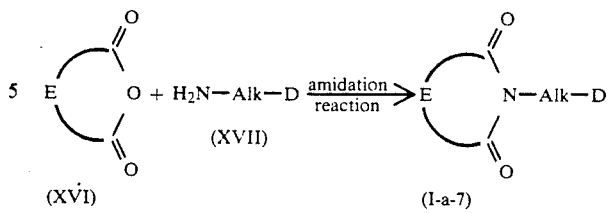

Said amidation reaction is generally carried out following the procedures described hereinabove for the preparation of (I) starting from (IV) and (V).

The compounds of formula (I) wherein L is a radical of formula (j) said compounds being represented by formula (I-a-8) may be prepared by a number of cyclization reactions known in the art for preparing hydantoin systems. For example, the compounds of formula (I-a-8) wherein $R^{23}$ and $R^{24}$ are both hydrogen, said compounds being represented by the formula (I-a-8-a), can be prepared by the cyclization reaction of an aldehyde or ketone of formula (XVIII) in the presence of potassium cyanide and ammonium carbonate.

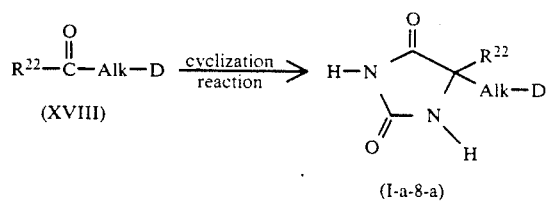

The compounds of formula (I) can alternatively be prepared by the reductive N-alkylation reaction of an appropriate ketone or aldehyde of formula $L'=O$ (XIX), said $L'=O$ being a compound of formula L-H wherein two geminal hydrogen atoms in said $C_{1-6}$alkanediyl or $C_{3-6}$cycloalkanediyl are replaced by $=O$, with a piperidine of formula H-D (II).

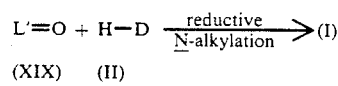

Said reductive N-alkylation reaction may conveniently be carried out by catalytically hydrogenating a mixture of the reactants in a suitable reaction-inert organic solvent according to art-known catalytic hydrogenating procedures. Suitable solvents are, for example, water; alkanols, e.g. methanol, ethanol, 2-propanol; cyclic ethers, e.g. 1,4-dioxane; halogenated hydrocarbons, e.g. trichloromethane; a dipolar aprotic solvent, e.g., N,N-dimethylformamide, dimethyl sulfoxide; or a mixture of such solvents. The term "art-known catalytic hydrogenating procedures" means that the reaction is carried out under hydrogen atmosphere in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g. thiophene and the like.

The compounds of formula (I) wherein $R^1$ is hydrogen and wherein the substituents in the 3- and 4-position of the piperidine ring have the trans configuration, said compounds being represented by the formula (I-b-1), may also be prepared by reacting a 7-oxa-3-azabicyclo[4.1.0]-heptane of formula (XX) with an amide of formula (XXI). The compounds of formula (I-b-1) can further be Q-alkylated or Q-acylated following art-known procedures thus preparing the corresponding compounds of formula (I-b-2) wherein the substituents in the 3- and 4-position of the piperidine ring have the trans configuration and wherein $R^1$ is other than hydrogen, said $R^1$ being represented by $R^{1-a}$.

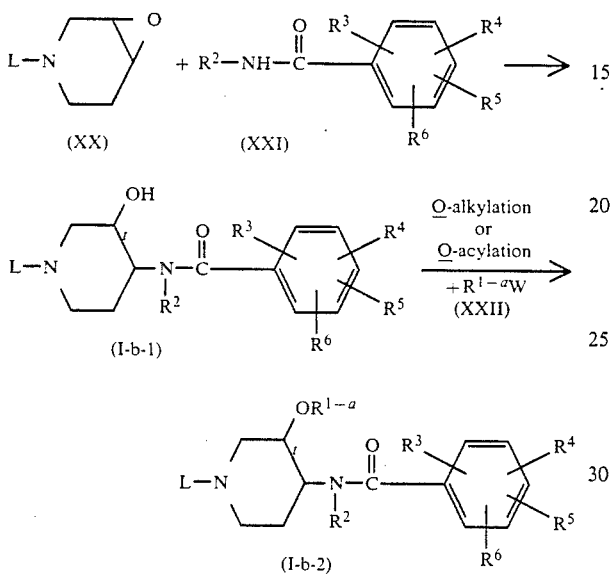

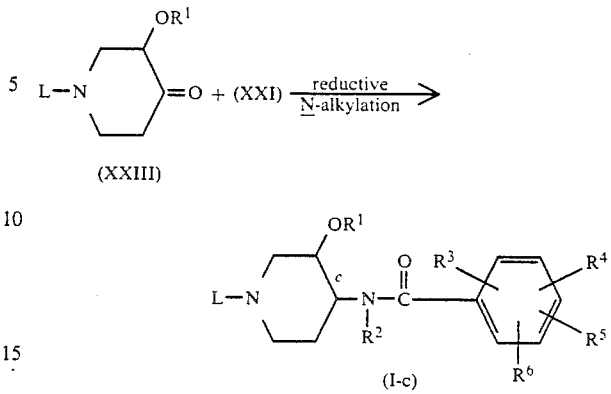

In (I-b-1) and (I-b-2) the symbol "t" indicates that the substituents in the 3- and 4- position of the piperidine ring are in trans configuration.

The reaction of (XX) with (XXI) may be conducted by stirring and, if desired, heating the reactants in a suitable reaction-inert solvent, such as, for example, an alcohol, e.g. methanol, ethanol and the like.

The Q-alkylation of Q-acylation reactions are conveniently conducted in an inert organic solvent such as, for example, an aromatic hydrocarbon, e.g. benzene, methylbenzene, dimethylbenzene, and the like; a ketone, e.g. 2-propanone, 4-methyl-2-pentanone and the like; an ether, e.g. 1,4-dioxane, 1,1'-oxybisethane, tetrahydrofuran and the like; or a dipolar aprotic solvent e.g. N,N-dimethylformamide, N,N-dimethylacetamide, dimethyl sulfoxide, 1-methyl-2-pyrrolidinone, and the like. An appropriate base such as, for example, an alkali metal carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein the substituents in the 3- and 4-position of the piperidine ring have the cis configuration, said compounds being represented by the formula (I-c), may also be prepared by the reductive N-alkylation of a piperidone of formula (XXIII) with an amide of formula (XXI).

In (I-c) the symbol "c" indicates that the substituents in the 3- and 4- position of the piperidine ring are in cis configuration. Said reductive N-alkylation reaction may be carried out by catalytically hydrogenating a mixture of reactants in a suitable reaction-inert solvent according to art-known catalytic hydrogenating procedures described hereinabove for preparing (I) from (XIX) and (II).

The compounds of formula (I) can also be converted into each other following art-known procedures of functional group transformation. Some examples of such procedures with be cited hereinafter.

The compounds of formula (I) having a nitro substituent may be converted into the corresponding amine by stirring and, if desired, heating the starting nitro-compounds in a hydrogen-containing medium in the presence of a suitable amount of an appropriate catalyst in the presence of a suitable solvent. Appropriate catalysts are, for example, platinum-on-charcoal, palladium-on-charcoal, Raney-nickel and the like catalyst. Suitable solvents are, for example relatively polar solvents such as, methanol, ethanol and the like.

The hydrogen atoms of the amino function(s) of compounds of formula (I) may be substituted following art-known procedures such as, for example, N-alkylation, N-acylation, reductive N-alkylation and the like methods.

1) Alkylcarbonyl, arylcarbonyl and the like groups may be introduced on the nitrogen atom by reacting the starting amine with an appropriate carboxylic acid or a derivative thereof such as, for example, an acid halide, acid anhydride and the like in a suitable solvent such as, for example, an aromatic hydrocarbon, e.g. benzene, a dipolar aprotic solvent, e.g. N,N-dimethylformamide or a mixture of such solvents.

2) Alkyl groups may be introduced by reacting the starting amine with an alkanal or alkanone under a hydrogen atmosphere in the presence of an appropriate catalyst such as, palladium-on-charcoal, platinum-on-charcoal and the like catalysts, in suitable solvent such as, methanol, ethanol and the like. In order to prevent the undesired further hydrogenation of certain functional groups in the reactants and the reaction products it may be advantageous to add an appropriate catalyst-poison to the reaction mixture, e.g. thiophene and the like.

The compounds of formula (I) containing a substituted amine may be converted into the corresponding compounds of formula (I) wherein said nitrogen bears a hydrogen following art-known methods for preparing NH groups. For example, where said nitrogen is substituted with $C_{1-6}$alkylcarbonyl, by treating the starting material with an aqueous acidic or basic solution optionally in admixture with an organic solvent.

Compounds of formula (I) containing a hydroxy function may be O-alkylated or O-acylated according to art-known procedures, e.g. by stirring the former with an appropriate acylating agent, e.g. an acid anhydride or appropriate alkylating agent, if desired, in the presence of sodium hydride.

The compounds of formula (I) containing an arylmethoxy substituent may be converted into the corresponding compounds of formula (I) containing a hydroxy function, following art-known catalytic hydrogenolysis procedures.

Compounds of formula (I) bearing a protective dioxolan ring may be deacetalized to yield the corresponding oxo compounds. Said deacetalization may be conducted following procedures widely known in the art such as, for example, by reacting the starting materials in an acidic aqueous medium.

The compounds of formula (I) may also be converted to the corresponding N-oxide forms following art-known procedures for converting a trivalent nitrogen to its N-oxide-form. Said N-oxidation reaction may generally be carried out by reacting the starting material of formula (I) with an appropriate organic or inorganic peroxide. Appropriate inorganic peroxides comprise, for example, hydrogen peroxide, an alkali metal or earth alkali metal peroxide, e.g. sodium peroxide, potassium peroxide, barium peroxide and the like; appropriate organic peroxides may comprise peroxy acids such as, for example, benzenecarboperoxoic acid or halo substituted benzenecarboperoxoic acid, e.g. 3-chlorobenzenecarboperoxoic acid and the like, peroxoalkanoic acids, e.g. peroxoacetic acid and the like, alkylhydroperoxides, e.g. t.butyl hydroperoxide and the like. Said N-oxidation may be carried out in a suitable solvent such as for example, water, lower alkanols, e.g. methanol, ethanol, propanol, butanol and the like, hydrocarbons, e.g. benzene, methylbenzene, dimethylbenzene and the like, ketones, e.g. 2-propanone, 2-butanone and the like, halogenated hydrocarbons, e.g. dichloromethane, trichloromethane and the like, and mixtures of such solvents. In order to enhance the reaction rate, it may be appropriate to heat the reaction mixture.

Some of the intermediates and starting materials in the foregoing preparations are known compounds while others are novel. They may be prepared according to art-known methodologies of preparing said known or similarly known compounds. Some procedures for preparing such intermediates will be described hereinafter in more detail.

The intermediates of formula (II) may be derived from an appropriately substituted piperidine of formula (XXIV) by reacting the latter with a reagent of formula (V) or a functional derivative thereof, following the amidation procedures described for the preparation of (I) starting from (IV) and (V), and subsequently removing of the protective group P in the thus obtained intermediate (XXV) following art-known procedures, e.g. by hydrolysis in an acidic or an alkaline aqueous medium or by catalytic hydrogenation, depending upon the nature of P.

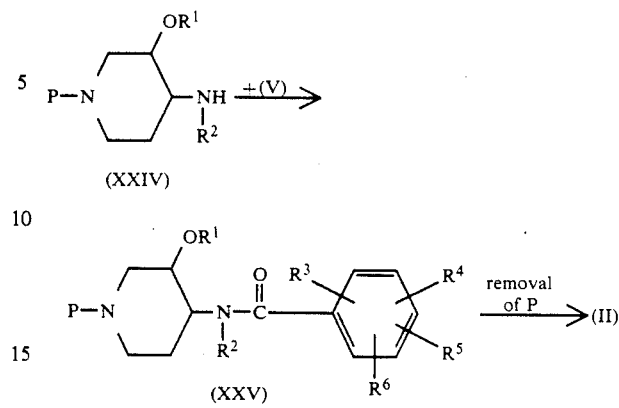

In the reaction of (XXIV) with (V) and in the following reaction schemes P represents a suitable protective group which is readily removeable by hydrogenation or hydrolysation. Preferred protective groups may for example be, hydrogenolyzable groups e.g. phenylmethyl and the like, and hydrolyzable groups e.g. $C_{1-6}$alkyloxycarbonyl and the like.

The intermediates of formula (IV) can be derived from an appropriately substituted piperidine of formula (XXVI) by alkylating the latter with an appropriate reagent, following the alkylation procedures described for (I) starting from (II) and (III) and, subsequently removing the protective group P in the thus obtained intermediate following art-known procedures described hereinbefore.

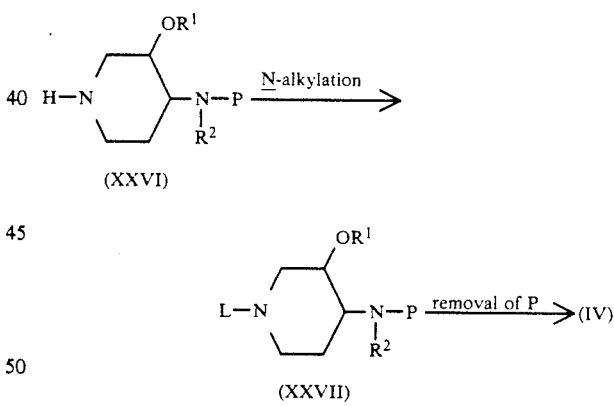

The intermediates of formula (XXIV), can easily be converted into the intermediates of formula (XXVI), for example, by introducing a protective group $P^1$ on the exocyclic amine function and selectively removing the protective group $P^2$ on the endocyclic amine function.

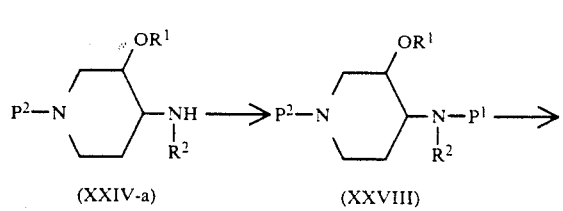

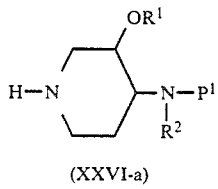

(XXVI-a)

$P^1$ and $P^2$ represents suitable protective groups as defined hereinbefore which are readily introduced and removed. Suitable protective groups are, for example, hydrogenolyzable groups as $P^1$ radicals, e.g. a phenylmethyl group and the like, and hydrolyzable groups as $P^2$ radicals, e.g. $C_{1-6}$alkyloxycarbonyl, a $C_{1-6}$alkylcarbonyl and the like. In general, the piperidines (VIII), (XXIV) and (XXVI) used as starting materials, can be prepared following procedures analogous to those described in Drug Development Research 8, 225-232 (1986) and in the Published Eur. Pat. Appl. No. 0,076,530 which corresponds to U.S. application Ser. No. 403,603, which are incorporated herein as reference.

From formula (I) it is evident that the compounds of this invention and some intermediates have at least two asymmetric carbon atoms in their structure.

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids or their optically activated derivatives.

It is evident that the cis and trans diastereomeric racemates may be further resolved into their optical isomers, cis(+), cis-(-), trans(+) and trans(-) by the application of methodologies known to those skilled in the art.

Pure stereochemically isomeric forms may also be derived from the corresponding pure stereochemically isomeric forms of the appropriate starting materials, provided that the reaction occurs stereospecifically.

The compounds of formula (I) containing an alkene moiety may be present in a "E" or "Z" form, said E- and Z-notation having the meanings described in J. Org. Chem., 35, 2849-2868 (1970).

Stereochemically isomeric forms of the compounds of formula (I) are naturally intended to be embraced within the scope of the invention.

The compounds of formula (I), the N-oxide forms, the pharmaceutically acceptable acid addition salts and possible stereoisomeric forms thereof possess favourable gastrointestinal motility stimulating properties. In particularly they show an accelerated gastric emptying. The latter property is clearly evidenced by the results obtained in the "Gastric emptying of a liquid meal in rats"-test described hereinafter.

The stimulatory effect of the subject compounds on the motility of the gastrointestinal system may further be evidenced by, for example, the "Amplification of contrations induced by submaximal transmural stimulation of Guinea pig ileum"-test described in The Journal of Pharmacology and Experimental Therapeutics, 234, 775-783 (1985) and the "Amplification of contrations induced by supramaximal transmural stimulation of Guinea pig ileum"-test both described hereinafter.

Similar experiments revealed that some compounds of formula (I), the N-oxide forms, the pharmaceutically acceptable acid addition salts and possible stereoisomeric forms antagonize the gastrointestinal relaxation as induced by several exogenous agonists.

In view of their useful gastrointestinal motility enhancing properties the subject compounds may be formulated into various forms for administration purposes.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large par, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spoton, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of their capability to stimulate the motility of the gastrointestinal system and, in particular their capacity to accelerate the gastric emptying, the subject compounds are useful to normalize or to improve the gastric and intestinal emptying in subjects suffering from a disturbed motility, e.g. a decreased peristalsis, of the oesophagus and/or stomach and/or small and/or large intestine.

In view of the utility of the compounds of the present invention, there is provided a method of treating warm-blooded animals suffering from motility disorders of the gastrointestinal system such as, for example, oesophagitis, gastroparesis, flatulent dyspepsia, non-ulcer dyspepsia, pseudo-obstruction, impaired colonic transit and the like disorders. Said method comprises the systemic administration of an effective gastrointestinal motor-stimulating amount of a compound of formula(I), a N-oxide, a pharmaceutically acceptable acid addition salt or a possible stereoisomeric form thereof, to warm-blooded animals.

Those of skill in the pertinent art could easily determine the effective motor-stimulating amount from the test results presented hereinafter.

In general it is contemplated that an effective amount would be from 0.001 mg/kg to 10 mg/kg body weight, and more preferably from 0.01 mg/kg to 1 mg/kg body weight.

The following examples are intended to illustrate and not to limit the invention in all its aspects. Unless otherwise stated all parts therein are by weight;

EXPERIMENTAL PART

A. Preparation of Intermediates

Example 1

To a stirred and cooled (ice bath) solution of 71.12 parts of pyrrolidine in 210 parts of petroleumether were added dropwise 70.5 parts of 4-chlorobutanoyl chloride at a temperature below 15° C. Upon completion, stirring was continued overnight at room temperature. Water was added. The product was extracted with dichloromethane. The extract was separated, dried, filtered and evaporated. The residue was distilled at 266 Pa bp. 137° C., yielding 45 parts (51%) of 1-(4-chloro-1-oxobutyl)pyrrolidine (int. 1).

In a similar manner there were also prepared:

| No. | s | $R^{15}$ | $R^{16}$ | $R^{25}$ | physical data |
|---|---|---|---|---|---|
| 2 | 2 | 2-H$_3$C— | H | H$_3$C— | bp. 135° C. at 199.5 Pa |
| 3 | 2 | 2-H$_3$C— | 6-H$_3$C— | H | bp. 95° C. at 5.32 Pa |
| 4 | 2 | 4-H$_3$C— | H | H | bp. 145° C. at 239.4 Pa |
| 5 | 2 | 2-H$_3$C— | H | H | bp. 146° C. at 266 Pa |
| 6 | 3 | H | H | H | bp. 95° C. at 13.3 Pa |
| 7 | 2 | 4-H$_2$N—C(O)— | H | H | — |
| 8 | 2 | 4-HO— | H | H | — |
| 9 | 2 | 4-C$_2$H$_5$O—C(O)— | H | H | — |
| 10 | 2 | 3-H$_2$N—C(O)— | H | H | — |
| 11 | 2 | 3-HO—CH$_2$— | H | H | — |
| 12 | 2 | 3-HO— | H | H | — |
| 13 | 2 | H | H | H$_3$C— | bp. 129° C. at 199.5 Pa |
| 14 | 2 | 4-(methyl-1,3-dioxolan-2-yl) | H | H | bp. 140° C. at 13.3 Pa |
| 15 | 1 | 2-C$_2$H$_5$O—C(O)— | H | H | bp. 172° C. at 199.5 Pa |
| 16 | 2 | 4-N(CH$_3$)$_2$— | H | H | .HCl |
| 17 | 2 | 3-N(CH$_3$)$_2$— | H | H | — |

| No. | A | $R^{17}$ | $R^{18}$ | —Alk—W | physical data |
|---|---|---|---|---|---|
| 18 | C$_6$H$_5$—N— | H | H | —(CH$_2$)$_3$—Cl | .HCl |
| 19 | (pyridin-2-yl)—N— | H | H | —(CH$_2$)$_3$—Cl | .HCl |
| 20 | CH$_3$—N— | H | H | —(CH$_2$)$_5$—Br | .HCl |
| 21 | n-C$_6$H$_{13}$—N— | H | H | —(CH$_2$)$_3$—Cl | .HCl |
| 22 | (pyridin-2-yl)—N— | H | H | —(CH$_2$)$_3$—Cl | .HCl |
| 23 | CH$_3$—N— | (2,3-dimethylphenyl) | | —(CH$_2$)$_3$—Cl | | and 8-(4-chloro-1-oxobutyl)-1,4-dioxa-8-azaspiro[4.5]-decane; bp. 120° C. at 5.32 Pa (int. 24).

Example 2 a) To a stirred mixture of 20 parts of 2-methyl-4-(phenylmethyl)piperazine, 11.13 parts of sodium carbonate and 120 parts of 2-propanone were added dropwise 16.28 parts of a 4-chloro-2-methylbutanoyl chloride. Upon completion, stirring was continued for 45 minutes. The precipitated product was filtered off and taken up in dichloromethane. Water and sodium carbonate were added. The organic layer was separated, dried, filtered and evaporated. The residue was converted into the hydrochloride salt in 2-propanol. The salt was filtered off and dried in vacuo at 40° C., yielding 16.5 parts (45.5%) of 1-(4-chloro-2-methyl-1-oxobutyl)-2-methyl-4-(phenylmethyl)piperazine monohydrochloride (int. 25).

b) A mixture of 16 parts of 1-(4-chloro-2-methyl-1-oxobutyl)-2-methyl-4-(phenylmethyl)piperazine monohydrochloride, 200 parts of methanol and 7 parts of a formaldehyde solution 40% was hydrogenated at normal pressure and at 60° C. with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia, (98:2 by volume) as eluent. The pure fractions were collected and the eluent was evaporated. The residue was converted into the hydrochloride salt in 2-propanol and 2,2'-oxybispropane, yielding 9 parts (72.6%) of 1-(4-chloro-2-methyl-1-oxybutyl)-2,4-dimethylpiperazine monohydrochloride (int. 26).

Example 3 a) A mixture of 24.2 parts of 3-methoxy-1-(phenylmethyl)-4-piperidinone, 16 parts of N-methylmethanamine, 1 part of a thiophene solution in methanol and 520 parts of methanol was hydrogenated at normal pressure and at 50° C. with 3 parts of palladium-on-charcoal catalyst 10%. After the calculated amount of hydrogen was taken up, the catalyst was filtered off and the filtrate was evaporated, yielding 27.3 parts (100%) of cis-3-methoxy-N,N-dimethyl-1-(phenylmethyl)-4-piperidinamine (int. 27).

b) A mixture of cis-3-methoxy-N,N-dimethyl-1-(phenylmethyl)-4-piperidinamine was hydrogenated at normal pressure and at room temperature with 5 parts of palladium-on-charcoal catalyst 10%. After the calculated amount of hydrogen was taken up, the catalyst was filtered off and the filtrate was evaporated, yielding 17 parts (100%) of cis-3-methoxy-N,N-dimethyl-4-piperidinamine (int. 28).

c) To a stirred and cooled (ice/bath) mixture of 7.9 parts of cis-3-methoxy-N,N-dimethyl-4-piperidinamine, 7 parts of N,N-diethylethanamine, 195 parts of dichloromethane were added dropwise 6.16 parts of 4-chlorobutanoyl chloride (temperature <5° C.). Upon completion, stirring was continued for 30 minutes. The organic layer was washed twice with a saturated sodium chloride solution, dried, filtered and evaporated. The residue was purified by column chromatography over silica gel using a mixture of trichloromethane and methanol (90:10 by volume) as eluent. The pure fractions were collected and the eluent was evaporated, yielding 13.7 parts (100%) of cis-1-(4-chloro-1-oxobutyl)-3-methoxy-N,N-dimethyl-4-piperidinamine (int. 29).

Example 4 a) To a stirred solution of 7.5 parts of 2-(methylamino)ethanol in 75 parts of trichloromethane were added 9.8 parts of N,N-diethylethanamine while cooling in an ice bath. A solution of 13.4 parts of 1-pyrrolidinecarbonyl chloride in 52.5 parts of trichloromethane was added dropwise (exothermic reaction, the temperature rose from −10° C. to ~0° C.). Upon complete addition, stirring was continued for 6 hours at room temperature. Another portion of 1.5 parts of 2-(methylamino)ethanol was added and stirring was continued over weekend at room temperature. The separated organic layer was washed with a hydrochloric acid solution 5% and water, dried, filtered and evaporated, yielding 7 parts (40.1%) of N-(2-hydroxyethyl)-N-methyl-1-pyrrolidinecarboxamide as a residue (int. 30).

b) To a stirred solution of 4 parts of N-(2-hydroxyethyl)-N-methyl-1-pyrrolidinecarboxamide in 22.5 parts of methylbenzene were added 2.9 parts of thionyl chloride. After the addition of a few drops of N,N-dimethylformamide, the reaction mixture was heated slowly to reflux temperature. After stirring for 2 hours at this temperature, the mixture was cooled and the whole was evaporated, yielding 4.5 parts (100%) of N-(2-chloroethyl)-N-methyl-1-pyrrolidinecarboxamide as a residue (int. 31).

In a similar manner there was also prepared:
(2-chloroethyl) 1-pyrrolidinecarboxylate as a residue (int. 32).

Example 5

To a stirred solution of 25 parts of 3-methyl-2,4-imidazolidinedione in 198 parts of N,N-dimethylformamide were added portionwise 1.6 parts of a sodium hydride dispersion 50%* under nitrogen atmosphere (exothermic reaction, cooling). Upon complete addition, stirring was continued for 1 hour at room temperature. 45.5 parts of 1,2-dibromoethane were added dropwise. Upon completion, the whole was stirred for 2 days at room temperature. The reaction mixture was evaporated and the residue was taken up in a mixture of water and dichloromethane. The separated organic layer was dried, filtered and evaporated. The residue was purified by column chromatography over silica gel using a mixture of trichloromethane and methanol (95:5 by volume) as eluent. The pure fractions were collected and the eluent was evaporated, yielding 35.8 parts (73.6%) of 3-(2-bromoethyl)-1-methyl-2,4-imidazolidinedione as a residue (int. 33).

In a similar manner there were also prepared:
1-(3-chloropropyl)-2-imidazolidinone as a residue (int. 34);
1-(4-chlorobutyl)-3-ethyl-1,3-dihydro-2H-benzimidazol-2-one (int. 35); and
1-(4-chlorobutyl)-3-ethyl-2-imidazolidinone as a residue (int. 36).

Example 6 a) A solution of 109 parts of bis(1,1-dimethylethyl) dicarbonate in 375 parts of trichloromethane was added dropwise to a solution of 40 parts of 4-(methylamino)-1-butanol in 750 parts of trichloromethane (slightly exothermic reaction). The reaction mixture was evaporated and the residue was distilled at 26.60 Pa, yielding 50 parts (57.2%) of (1,1-dimethylethyl) (4-hydroxybutyl)methylcarbamate (int. 37).

b) A solution of 50 parts of (1,1-dimethylethyl) (4-hydroxybutyl)methylcarbamate in 91 parts of dichloromethane was added dropwise to a mixture of 150 parts of pyridinium dichromate, 112 parts of molecular sieves and 1300 parts of dichloromethane at a temperature about 10° C. Upon completion, stirring was continued for 3 hours at room temperature. The reaction mixture was filtered, washed with 1,1'-oxybisethane and the filtrate was evaporated. The residue was purified by column chromatography over silica gel using dichloromethane as eluent. The pure fractions were collected and the eluent was evaporated with methylbenzene, yielding 35 parts (70%) of (1,1-dimethylethyl) methyl(4-oxobutyl)carbamate as a residue (int. 38).

In a similar manner there were also prepared:
(1,1-dimethlethyl) methyl(3-oxopropyl)carbamate as a residue (int. 39); and
(1,1-dimethylethyl) methyl(2-oxoethyl)carbamate as a residue (int. 40).

Example 7

Gaseous carbonic dichloride was bubbled during 3 hours through a solution of 83 parts of 2-amino-3,4,5-trimethoxybenzoic acid in 63 parts of concentrated hydrochloric acid and 525 parts of water (the temperature rose to 40° C.). The precipitated product was filtered off, washed with water and dried in vacuo, yielding 60.5 parts (75%) of 6,7,8-trimethoxy-2H-3,1-benzoxazine -2,4(1H)-dione; mp. 247.3° C. (int. 41).

Example 8 a) A mixture of 43.9 parts of 1-(4-chloro-1-oxobutyl)pyrrolidine, 55.1 parts of cis-3-methoxy-N-(phenylmethyl)-4-piperidinamine, 37.8 parts of N,N-diethylethanamine and 900 parts of N,N-dimethylformamide was stirred overnight at 70° C. Another portion of 4.4 parts of 1(4-chloro-1-oxobutyl)pyrrolidine was added and stirring was continued overnight at 70° C. The reaction mixture was evaporated and the residue was taken up in a mixture of water and sodium carbonate. The product was extracted with dichloromethane. The extract was washed with water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated, yielding 53.1 parts (59.0%) of cis-1-[4-[3-methoxy-4-[(phenylmethyl)amino]-1-piperidinyl]-1-oxobutyl]pyrrolidine as a residue (int. 42).

b) A mixture of 53 parts of cis-1-[4-[3-methoxy-4-[(phenylmethyl)amino]-1-piperidinyl]-1-piperidinyl]-1-oxobutyl]pyrrolidine and 200 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia, (95:5 by volume) as eluent. The pure fractions were collected and the eluent was evaporated, yielding 28.3 parts (71.4%) of cis-1-[4-(4-amino-3-methoxy-1-piperidinyl)-1-oxobutyl]pyrrolidine as a residue (int. 43).

In a similar manner there was also prepared:
cis-N-[2-(4-amino-3-hydroxy-1-piperidinyl)ethyl]-N-methyl-1-pyrrolidinecarboxamide as a residue (int. 44).
cis-1-[2-(4-amino-3-methoxy-1-piperidinyl)ethyl]-3-ethyl-2-imidazolidinone as a residue (int. 45).

Example 9 a) A mixture of 183.4 parts of ethyl cis-3-methoxy-4-[(phenylmethyl)amino]-1-piperidinecarboxylate, 144 parts of (chloromethyl)benzene, 85 parts of sodium carbonate and 720 parts of methylbenzene was stirred for 10 days at reflux temperature. The reaction mixture was filtered and the filtrate was washed three times with 400 parts of water, dried, filtered and evaporated. Petroleumether was added. The whole was cooled whereupon the product solidified. It was filtered off and crystallized from petroleumether. The product was filtered off and dried in vacuo at 40° C., yielding 155 parts (64%) of ethyl cis-4-[bis(phenylmethyl)amino]-3-methoxy-1-piperidinecarboxylate; mp. 95.2° C. (int. 46).

b) To a stirred mixture of 230 parts of potassium hydroxide and 1600 parts of 2-propanol was added 155 parts of ethyl cis-4-[bis(phenylmethyl)amino]-3-methoxy-1-piperidinecarboxylate. The whole was stirred and refluxed for 7 hours. The reaction mixture was evaporated. Water was added and the mixture was evaporated till all traces of 2-propanol were removed. The product was extracted with dichloromethane. The extract was washed twice with a sodium chloride solution in water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was taken up in dichloromethane. The solution was washed with a sodium hydroxide solution 5%, dried, filtered and evaporated, yielding 70 parts (55%) of cis-3-methoxy-N,N-bis(phenylmethyl)-4-piperidinamine as a residue (int. 47).

c) Through a stirred solution of 70 parts of cis-3-methoxy-N,N-bis(phenylmethyl)-4-piperidinamine in 368 parts of ethanol and 460 parts of water was bubbled gaseous oxirane for 1.5 hour at room temperature. The whole was stirred overnight at room temperature. The product was filtered off, washed with a mixture of ethanol and water (50:50 by volume) and crystallized from acetonitrile. The product was filtered off and dried in vacuo at 40° C., yielding 50 parts (61.3%) of cis-4-[bis(phenylmethyl)amino]-3-methoxy-1-piperidineethanol (int. 48).

d) To a stirred mixture of 5.32 parts of cis-4-[bis(phenylmethyl)amino]-3-methoxy-1-piperidineethanol and 96 parts of dichloromethane were added 3.63 parts of phenyl carbonochloridate while cooling. The whole was stirred for 35 hours at room temperature. The reaction mixture was evaporated. The residue was solidified in 2,2'-oxybispropane. The product was filtered off and dried, yielding 6.4 parts (83.4%) of cis-[2-[4-[bis(phenylmethyl)amino]-3-methoxy-1-piperidinyl]ethyl]phenylcarbonate monohydrochloride (int. 49).

e) To a stirred suspension of 6.4 parts of cis-[2-[4-[bis(phenylmethyl)amino]-3-methoxy-1-piperidinyl]ethyl]phenylcarbonate monohydrochloride in 105 parts of 1,1'-oxybisethane was added 200 parts of ammonia. After 48 hours, the 1,1'-oxybisethane layer was treated with a sodium hydroxide solution 5%. The reaction mixture was poured into water. The product was filtered off and crystallized from acetonitrile. The product was filtered off and dried in vacuo at 50° C., yielding 2.13 parts (38.2%) of cis-[2-[4-[bis(phenylmethyl)amino]-3-methoxy-1-piperidinyl]ethyl]carbamate; mp. 162.2° C. (int. 50).

f) A mixture of 16.3 parts of cis-[2-[4-[bis(phenylmethyl)amino]-3-methoxy-1-piperidinyl]ethyl]carbamate and 200 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 8.5 parts (95.4%) of cis-[2-(4-amino-3-methoxy-1-piperidinyl)ethyl]carbamate as a residue (int. 51).

B. Preparation Of Final Compounds

Example 10

A mixture of 2.21 parts of 1-(2-chloroethyl)-3-ethyl-2-imidazolidinone, 3.13 parts of cis-4-amino-5-chloro-2-methoxy-N-(3-methoxy-4-piperidinyl)benzamide, 1.58 parts of sodium carbonate and 90 parts of N,N-dimethylformamide was stirred and heated for 48 hours at 70° C. The reaction mixture was evaporated. Water was added and the product was extracted twice with dichloromethane. The combined extracts were washed with water, dried, filtered and evaporated. The residue was purified by column chromatography over silica gel using a mixture of trichloromethane and methanol, saturated with ammonia, (95:5 by volume) as eluent. The first fraction was collected and the eluent was evaporated. The residue was crystallized from acetonitrile. The product was filtered off and dried, yielding 3.08 parts (67.8%) of cis-4-amino-5-chloro-N-[1-[2-(3-ethyl-2-oxo-1-imidazolidinyl)ethyl]-3-methoxy-4-piperidinyl]-2-methoxybenzamide; mp. 152.8° C. (compound 1).

In a similar manner there were also prepared:

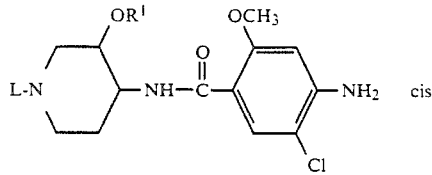

| Comp. No. | L | R¹ | base/salt | mp. (°C.) |
|---|---|---|---|---|
| 2 | CH₃—N(OCH₃)—C(=O)—(CH₂)₃— | CH₃ | base | 174.8 |
| 3 | cyclohexyl-C(=O)-O-(CH₂)₂— | CH₃ | base | 67.1 |
| 4 | H₃C—N(C(=O))N—CH₂—CH₂— (imidazolidinone) | CH₃ | base | 180.6 |
| 5 | H₃C—CH₂—N(C(=O))N—CH₂—CH₂— (benzimidazolone) | CH₃ | base | 128.9 |
| 6 | 2-oxopyrrolidinyl-N—C(=O)—(CH₂)₃— | CH₃ | base | 105.6 |
| 7 | CH₃—N(C(=O))N—CH₂—CH₂— (benzimidazolone) | CH₃ | HCl.H₂O | 203.5 |
| 8 | 3,4,5-(H₃CO)₃—C₆H₂—C(=O)—O—(CH₂)₃— | CH₃ | H₂O | 120.0 |
| 9 | morpholinyl-N—C(=O)—CH₂— | CH₃ | H₂O | 152.2 |
| 10 | pyrrolidinyl-N—C(=O)—(CH₂)₃— | C₂H₅ | base | 176.9 |

-continued

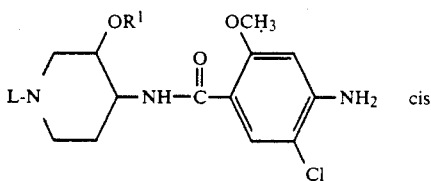

| Comp. No. | L | R¹ | base/salt | mp. (°C.) |
|---|---|---|---|---|
| 11 | H₅C₂—N⟨(C=O)N⟩—CH₂—CH₂— | H | base | |

Example 11

A mixture of 6.3 parts of 1-(3-chloropropyl)-3-ethyl-2-imidazolidinone, 4.76 parts of cis-4-amino-5-chloro-2-methoxy-N-(3-methoxy-4-piperidinyl)benzamide, 2.3 parts of sodium carbonate, 0.1 parts of potassium iode and 90 parts of N,N-dimethylacetamide was stirred over weekend at 70° C. After cooling, the reaction mixture was evaporated. The residue was taken up in dichloromethane and water. The organic layer was separated, washed twice with water, dried, filtered and evaporated. The residue was purified by column chromatography over silica gel using a mixture of trichloromethane and methanol (96:4 by volume) as eluent. The pure fractions were collected and the eluent was evaporated. The residue was crystallized from acetonitrile and a few drops of water at 0° C. The product was filtered off and dried in vacuo at 40° C., yielding 2.83 parts (36.6%) of cis-4-amino-5-chloro-N-[1-[3-(3-ethyl-2-oxo-1-imidazolidinyl)propyl]-3-methoxy-4-piperidinyl]-2-methoxybenzamide; mp. 112.9° C. (compound 12).

In a similar manner there were also prepared:
cis-4-amino-5-chloro-N-[1-[4-(3-ethyl-2-oxo-1-imidazolidinyl)butyl]-3-methoxy-4-piperidinyl]-2-methoxybenzamide; mp. 84.2° C. (compound 13); and
cis-4-amino-5-chloro-N-[3-ethoxy-1-[2-(3-ethyl-2-oxo-1-imidazolidinyl)ethyl]-4-piperidinyl]-2-methoxybenzamide; mp. 161.8° C. (compound 14).

Example 12

To a stirred solution of 3.00 parts of 1-(4-chloro-1-oxobutyl)pyrrolidine in 67.5 parts of N,N-dimethylformamide were added 1.93 parts of trans-4-amino-5-chloro-N-(3-hydroxy-4-piperidinyl)-2-methoxybenzamide and 1.5 parts of N,N-diethylethanamine and the whole was stirred for 18 hours at 70° C. The reaction mixture was evaporated and the residue was taken up in a sodium carbonate solution in water. The product was extracted with trichloromethane. The extract was washed with water, dried, filtered and evaporated. The residue was purified by column chromatography over silica gel using a mixture of trichloromethane and methanol, saturate with ammonia, (90:10 by volume) as eluent. The pure fractions were collected and the eluent was evaporated. The residue was crystallized from acetonitrile. The product was filtered off and dried, yielding 2.1 parts (47.8%) of trans-4-amino-5-chloro-N-[3-hydroxy-1-[4-oxo-4(1-pyrrolidinyl)butyl]-4-piperidinyl]-2-methoxybenzamide; mp. 174.7° C. (compound 15).

In a similar manner there were also prepared:
cis-4-amino-5-chloro-N-[1-[2-(2,5-dioxo-1-imidazolidinyl)ethyl]-3-methoxy-4-piperidinyl]-2-methoxybenzamide monohydrate; mp. 220.4° C. (compound 16);
cis-[2-[4-[(4-amino-5-chloro-2-methoxybenzoyl)amino]-3-methoxy-1-piperidinyl]ethyl] 1-pyrrolidinecarboxylate; mp. 170.6° C. (compound 17);
trans-4-amino-5-chloro-2-methoxy-N-[3-methoxy-1-[4-oxo-4-(1-pyrrolidinyl)butyl]-4-piperidinyl]benzamide monohydrate; mp. 101.1° C. (compound 18);
cis-4-amino-5-chloro-2-methoxy-N-[3-methoxy-1-[2-[3-methyl-2,5-dioxo-1-imidazolidinyl)ethyl]-4-piperidinyl]benzamide monohydrate; mp. 121.0° C.(compound 19);
cis-4-amino-5-chloro-2-methoxy-N-[3-methoxy-1-[4-(4-methyl-1-piperazinyl)-4-oxobutyl]-4-piperidinyl]benzamide; mp. 175.9° C. (compound 20);
cis-4-amino-5-chloro-N-[3-hydroxy-1-[4-oxo-4-(1-pyrrolidinyl)butyl]-4-piperidinyl]-2-methoxybenzamide as a residue (compound 21); and
cis-4-amino-5-chloro-2-methoxy-N-[3-methoxy-1-[2-(4-methyl-1-piperazinyl)-2-oxoethyl]-4-piperidinyl]benzamide hemihydrate; mp. 140.6° C. (compound 22).

Example 13

A mixture of 2.54. parts of 4-chloro-N-methyl-N-phenylbutanamide, 3.14 parts of cis-4-amino-5-chloro-2-methoxy-N-(3-methoxy-4-piperidinyl)benzamide, 2.45 parts of N,N-diethylethanamine, 0.1 parts of potassium iodide and 90 parts of N,N-dimethylformamide was stirred for 20 hours at 80° C. The reaction mixture was evaporated. The residue was taken up in water and sodium carbonate. The product was extracted with dichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from acetonitrile and a small amount of water. The product was filtered off and dried, yielding 2.05 parts (40.4%) of cis-4-[(4-amino-5-chloro-2-methoxybenzoyl)amino]-3-methoxy-N-methyl-N-phenyl-1-piperidinebutanamide monohydrate; mp. 97.4° C. (compound 23).

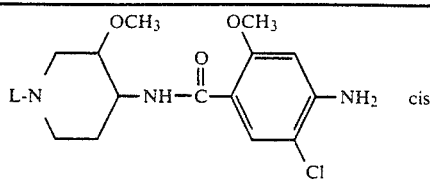

| Comp. No. | L | base/salt | mp. (°C.) |
|---|---|---|---|
| 24 | CH₃—C(=O)—O—(CH₂)₂— | base | 151.7 |
| 25 | HN⌐NH—N—CH₂—CH₂— (imidazolidinone) | base | 200.0 |
| 26 | (imidazolidinone)N—CH₂—CH₂—CH₂— | 1½ H₂O | 96.8–100.7 |
| 27 | (CH₃)₂CH—C(=O)—O—(CH₂)₂— | base | 126.8 |
| 28 | H₂N—C(=O)—(piperidine)N—C(=O)—(CH₂)₃— | base | 103.6 |
| 29 | HO—(piperidine)N—C(=O)—(CH₂)₃— | base | 188.2 |
| 30 | H₅C₂—O—C(=O)—(piperidine)N—C(=O)—(CH₂)₃— | base | 141.8 |
| 31 | (pyrrolidine with CO-O-CH₂-CH₃)N—C(=O)—(CH₂)₃— | base | 151.3 |
| 32 | (3,3-dimethylglutarimide)N—(CH₂)₄— | base | 133.7 |
| 33 | Ph—(piperazine)N—C(=O)—(CH₂)₃— | base | 104.9 |
| 34 | 2-pyridyl—(piperazine)N—C(=O)—(CH₂)₃— | base | 164.2 |
| 35 | H₃C—N(piperazine)N—C(=O)—(CH₂)₄— | H₂O | 114.3 |

-continued

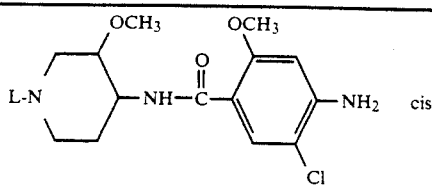

| Comp. No. | L | base/salt | mp. (°C.) |
|---|---|---|---|
| 36 | H₃C—N(piperazine)N—C(O)—(CH₂)₅— | base | 183.7 |
| 37 | H₃C—(CH₂)₅—N(piperazine)N—C(O)—(CH₂)₃— | base | 178.2 |
| 38 | H₃C—N(piperazine)—CH(CH₃)—N—C(O)—CH(CH₃)—(CH₂)₂— | 2 HCl 1.5 H₂O | 191.0 |
| 39 | pyrimidin-2-yl-N(piperazine)N—C(O)—(CH₂)₃— | base | 210.8 |
| 40 | (H₃C)₂N—(piperidine)N—C(O)—(CH₂)₃— | base | 236.0 |
| 41 | (H₃C)₂N—(3-methoxypiperidine)N—C(O)—(CH₂)₃— | base | 159.1 |
| 42 | (H₃C)₂N—(3-piperidinyl)N—C(O)—(CH₂)₃— | 0.5 H₂O | 134.3 |
| 43 | H₃C—N(ethyl)-(o-phenylene)-N—C(O)—(CH₂)₃— | 1.5 H₂O | 115.8 |
| 44 | pyrrolidinyl-N—C(O)—N(CH₃)—(CH₂)₂— | base | 141.8 |

In a similar manner there was also prepared:
cis-4-amino-5-chloro-N-[3-ethoxy-1-]2-[methyl(1-pyrrolidinylcarbonyl)amino]ethyl]-4-piperidinyl]-2-methoxybenzamide hemihydrate; mp. 82.7° C. (compound 45)

In a similar manner there is also prepared:
cis-4-amino-5-chloro-N-[1-[4-(hexahydro-4-methyl-1H-1,4-diazepin-1-yl)-4-oxobutyl]-3-methoxy-4-piperidinyl]-2-methoxybenzamide (compound 46).

Example 14

A mixture of 4.5 parts of cis-4-amino-5-chloro-2-methoxy-N-(3-methoxy-4-piperidinyl)benzamide, 2.12 parts of sodium carbonate, 0.1 parts of potassium iodide and 120 parts of 4-methyl-2-pentanone was stirred and refluxed for 15 minutes using a water separator. Then there were added 3.92 parts of 1-(4-chloro-1-oxobutyl)-2,6-dimethylpiperidine and stirring was continued first for 3 hours at reflux and then overnight at room temperature. Water was added. The product was filtered off and purified by column chromatography over silica gel using a mixture of trichloromethane and methanol (90:10 by volume) as eluent. The pure fractions were collected and the eluent was evaporated. The residue was crystallized from acetonitrile. The product was filtered off and dried, yielding 5.25 parts (70.7%) of cis-4-amino-5-chloro-N-[1-[4-(2,6-dimethyl-1-piperidinyl)-4-oxobutyl]-3-methoxy-4-piperidinyl]-2-methoxybenzamide; mp. 202.1° C. (compound 47).

In a similar manner there were also prepared:

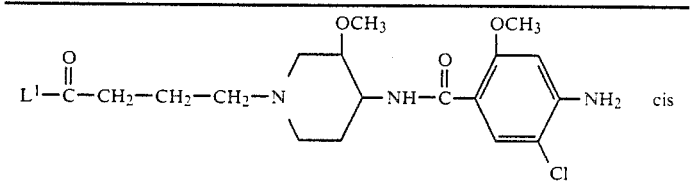

| Comp. No. | L¹ | base/salt | mp. (°C.) |
|---|---|---|---|
| 48 | 1-pyrrolidinyl | base | 202.7 |
| 49 | 4-morpholinyl | base | 191.9 |
| 50 | 1-piperidinyl | base | 187.0–187.2 |
| 51 | 4-methyl-1-piperidinyl | base | 199.0 |
| 52 | 2-methyl-1-piperidinyl | base | 178.6 |
| 53 | hexahydro-1H-azepin-1-yl | base | 176.7 |
| 54 | 3-(aminocarbonyl)-1-piperidinyl | H₂O | 107.1 |
| 55 | 3-(hydroxymethyl)-1-piperidinyl | base | 95.9 |
| 56 | 1,4-dioxa-8-azaspiro[4.5]dec-8-yl | base | 182.4 |
| 57 | 3-hydroxy-1-piperidinyl | H₂O | 94.6 |
| 58 | 4-(2-methyl-1,3-dioxolan-2-yl)-1-piperidinyl | base | 177.7 | cis-4-amino-5-chloro-N-[3-methoxy-1-[4-oxo-4-(1-piperidinyl)butyl]-4-piperidinyl]2-methoxybenzamide; mp. 148.6° C. (compound 59);

cis-4-amino-5-chloro-2-methoxy-N-[3-methoxy-1-[3-oxo-3-(1-piperidinyl)propyl]-4-piperidinyl]benzamide; mp. 194.7° C. (compound 60);

cis-4-amino-5-chloro-2-methoxy-N-[3-methoxy-1-[3-methyl-4-oxo-4-(1-piperidinyl)butyl]-4-piperidinyl]-benzamide; mp. 181.2° C. (compound 61);

cis-4-amino-5-chloro-2-methoxy-N-[3-methoxy-1-[5-oxo-5-(1-piperidinyl)pentyl]-4-piperidinyl]benzamide; mp. 70.9° C. (compound 62);

(E)-cis-4-amino-5-chloro-2-methoxy-N-[3-methoxy-1-[4-oxo-4-(1-piperidinyl)-2-butenyl]-4-piperidinyl]benzamide; mp. 162.8° C. (compound 63);

cis-4-amino-5-chloro-2-methoxy-N-[3-methoxy-1-[3-methyl-4-(2-methyl-1-piperidinyl)-4-oxobutyl]-4-piperidinyl]benzamide ethanedioate (1:1), hemihydrate; mp. 182.7° C. (compound 64);

cis-4-amino-5-chloro-N-[1-[3-(3-ethyl-2,3-dihydro-2-oxo-1H-benzimidazol-1-yl)propyl]-3-methoxy-4-piperidinyl]-2-methoxybenzamide monohydrate; mp. 103.4° C. (compound 65); and cis-4-amino-5-chloro-N-[1-[4-(3-ethyl-2,3-dihydro-2-oxo-1H-benzimidazol-1-yl)butyl]-3-methoxy-4-piperidinyl]-2-methoxybenzamide hemidyrate; mp. 103.4° C. (compound 66).

Example 15

To a stirred solution of 4.04 parts of cis-1-[4-(4-amino-3-methoxy-1-piperidinyl)-1-oxobutyl]pyrrolidine in 225 parts of trichloromethane was added a solution of 4.15 parts of 3-chloro-5-ethyl-6-hydroxy-2-methoxybenzoyl chloride in trichloromethane. After stirring for 15 minutes at room temperature, 1.9 parts of N,N-diethylethanamine were added and the whole was stirred overnight at room temperature. The reaction mixture was washed with water, saturated with ammonia and twice with water, dried, filtered and evaporated. The residue was purified by column chromatography over silica gel using a mixture of trichloromethane and methanol, saturated with ammonia (90:10 by volume) as eluent. The pure fractions were collected and the eluent was evaporated. The residue was crystallized from 2,2'-oxybispropane. The product was filtered off and dried, yielding 5.2 parts (71.9%) of cis-3-chloro-5-ethyl-6-hydroxy-2-methoxy-N-[3-methoxy-1-[4-oxo-4-(1-pyrrolidinyl)-butyl]-4-piperidinyl]benzamide; mp. 90.8° C. (compound 67).

In a similar manner there were also prepared:

cis-3-bromo-2-hydroxy-6-methoxy-N-[3-methoxy-1-[4-oxo-4-(1-pyrrolidinyl)butyl]-4-piperidinyl]benzamide; mp. 134.5° C. (compound 68);

cis-3-bromo-5-chloro-2-hydroxy-6-methoxy-N-[3-methoxy-1-[4-oxo-4-(1-pyrrolidinyl)butyl]-4-piperidinyl]benzamide; mp. 127.7° C. (compound 69);

cis-2,5-dichloro-N-[3-methoxy-1-[4-oxo-4-(1-pyrrolidinyl)butyl]-4-piperidinyl]benzamide hemihydrate; mp. 156.2° C. (compound 70);

cis-5-(1,1-dimethylethyl)-2-hydroxy-N-[3-methoxy-1-[4-oxo-4-(1-pyrrolidinyl)butyl]-4-piperidinyl]benzamide; mp. 100.0° C. (compound 71);

and cis-N-[3-methoxy-1-[4-oxo-4-(1-pyrrolidinyl)butyl]-4-piperidinyl]-3-(trifluoromethyl)benzamide ethanedioate (1:1); mp. 183.6° C. (compound 72).

Example 16

To a stirred and cooled (<5° C.) suspension of 4.84 parts of 4-amino-5-chloro-2-methoxybenzoic acid in 90 parts of trichloromethane were added dropwise first 2.34 parts of N,N-diethylethanamine and then 2.56 parts of ethyl carbonochloridate at <5° C. Upon completion, stirring was continued for 45 minutes in an ice bath. This solution was added to a solution of 4.35 parts of cis-[2-(4-amino-3-methoxy-1-piperidinyl)ethyl]carbamate in 60 parts of trichloromethane at a temperature below 5° C. The mixture was stirred for 5 hours at room temperature. The product was filtered off (and set aside) and the filtrate was washed with a sodium carbonate solution in water. From the organic layer, the precipitated product was filtered off and together with the product, which was set aside (see above), crystallized from acetonitrile. The product was filtered off and dried in vacuo at 40° C., yielding 3.67 parts (43.8%) of cis-[2-[4-[(4-amino-5-chloro-2-methoxybenzoyl)amino]-3-methoxy-1-piperidinyl]ethyl]carbonate monohydrate; mp. 166.8° C. (compound 73).

In a similar manner there were also prepared:
cis-4-amino-2-methoxy-N-[3-methoxy-1-[4-oxo-4-(1-pyrrolidinyl)butyl]-4-piperidinyl]-5-[(methylamino)-sulfonyl]benzamide monohydrate; mp. 217.2° C. (compound 74);
cis-5-chloro-2-methoxy-N-[3-methoxy-1-[4-oxo-4-(1-pyrrolidinyl)butyl]-4-piperidinyl]-4-(methylamino)-benzamide; mp. 170.4° C. (compound 75);
cis-4-amino-2-ethoxy-N-[3-methoxy-1-[4-oxo-4-(1-pyrrolidinyl)butyl]-4-piperidinyl]-5-nitrobenzamide; mp.170.7° C. (compound 76);
cis-N-[2-[4-[(4-amino-5-chloro-2-methoxybenzoyl)amino]-3-hydroxy-1-piperidinyl]ethyl]-N-methyl-1-pyrrolidinecarboxamide (compound 77); and
cis-4-amino-N-[1-[2-(3-ethyl-2-oxo-1-imidazolidinyl)ethyl]-3-methoxy-4-piperidinyl]-2-methoxy-5-[(methylamino)sulfonyl]benzamide; mp. 224.4° C. (compound 78).

Example 17

To a stirred solution of 2.69 parts of cis-1-[4-(4-amino-3-methoxy-1-piperidinyl)-1-oxobutyl]pyrrolidine in 45 parts of methylbenzene and 72 parts of N,N-dimethylformamide were suspended 2.79 parts of 6,7,8-trimethoxy-2H-3,1-benzoxazine-2,4(1H)-dione. After stirring overnight at room temperature, the reaction mixture was evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the hydrochloride salt in 2-propanol. The whole was evaporated to dry and the residue was crystallized from acetonitrile. The product was filtered off and dried, yielding 3.48 parts (72.8%) of cis-2-amino-3,4,5-trimethoxy-N-[3-methoxy-1-[4oxo-4-(1-pyrrolidinyl)butyl]-4-piperidinyl benzamide dihydrochloride.monohydrate; mp. 176.5° C. (compound 79).

Example 18

To a stirred and cooled solution (5° C.) of 3.99 parts of cis-4-amino-N-[1-(2-aminoethyl)-3-methoxy-4-piperidinyl]-5-chloro-2-methoxybenzamide in 90 parts of trichloromethane were added 1.32 parts of N,N-diethylethanamine. Then there was added dropwise a solution of 1.18 parts of dimethylcarbamic chloride in 60 parts of trichloromethane at a temperature below 5° C. Upon completion, stirring was continued first for one hour while cooling in an ice bath and further for 40 hours at room temperature. The reaction mixture was washed successively with water, sodium carbonate solution in water, and water, dried, filtered and evaporated. The product was filtered off and crystallized from acetonitrile, yielding 3.12 parts (73%) of cis-4-amino-5-chloro-N-[1-[2-[(dimethylamino)carbonylamino]ethyl]-3-methoxy-4-piperidinyl]-2-methoxybenzamide; mp. 206.5° C. (compound 80).

In a similar manner there were also prepared:
ethyl cis-[2-[4-[(4-amino-5-chloro-2-methoxybenzoyl)amino]-3-methoxy-1-piperidinyl]ethyl]carbamate; mp. 164.7° C. (compound 81);
cis-4-amino-5-chloro-N-[1-[2-[(dibutylamino)carbonylamino]ethyl]-3-methoxy-4-piperidinyl]-2-methoxybenzamide; mp. 139.5° C. (compound 82);
cis-α-[[2-[4-[(4-amino-5-chloro-2-methoxybenzoyl)amino]-3-methoxy-1-piperidinyl]ethyl]aminocarbonyl]benzenemethanol acetate (ester); mp. 100.3° C. (compound 83);
cis-N-[2-[4-[(4-amino-5-chloro-2-methoxybenzoyl)amino]-3-methoxy-1-piperidinyl]ethyl]-4-methyl-1-piperazinecarboxamide; mp. 220.5° C. (compound 84);
cis-N-[2-[4-[(4-amino-5-chloro-2-methoxybenzoyl)amino]-3-methoxy-1-piperidinyl]ethyl]-N,4-dimethyl-1-piperazinecarboxamide; mp. 135.1° C. (compound 85); and
cis-N-[4-[4-[(4-amino-5-chloro-2-methoxybenzoyl)amino]-3-methoxy-1-piperidinyl]butyl]-N-methyl-1-pyrrolidinecarboxamide monohydrate; mp. 106.7° C. (compound 86).

Example 19

To a stirred suspension of 2.99 parts of α-(hydroxymethyl)benzeneacetic acid in 60 parts of trichloromethane were added dropwise first 1.82 parts of N,N-diethylethanamine and then 1.95 parts of ethyl carbonochloridate at a temperature below 5° C. Upon completion, stirring was continued for 45 minutes at this low temperature. The thus obtained solution was added dropwise to a solution of 5.35 parts of cis-4-amino-N-[1-(2-aminoethyl)-3-methoxy-4-piperidinyl]-5-chloro-2-methoxybenzamide in 45 parts of trichloromethane while the temperature was kept below 10° C. Upon completion, the whole was stirred for 20 hours at room temperature. The organic layer was washed with a sodium carbonate solution in water and with water, dried, filtered and evaporated. The residue was purified by column chromatography over silica gel using a mixture of trichloromethane and methanol, saturated with ammonia, (98:2 by volume) as eluent. The pure fractions were collected and the eluent was evaporated. The residue was crystallized from acetonitrile and a few drops of water. The product was filtered off and dried in vacuo at 30° C., yielding 0.76 parts (10.0%) of cis-N-[2-[4-[(4-amino-5-chloro-2-methoxybenzoyl)amino]-3-methoxy-1-piperidinyl]ethyl]-α-(hydroxymethyl)benzeneacetamide; mp. 114.0° C. (compound 87).

Example 20

A mixture of 1.85 parts of 1,3-isobenzofurandione, 4.4 parts of cis-4-amino-N-[1-(3-aminopropyl)-3-methoxy-4-piperidinyl]-5-chloro-2-methoxybenzamide and 45 parts of methylbenzene was stirred for 3 hours at reflux temperature, using a water separator. The reaction mixture was evaporated. The residue was taken up in trichloromethane. The organic phase was washed with a saturate solution of sodium carbonate and water, dried, filtered and evaporated. The residue was purified by column chromatography over silica gel using a mixture of trichloromethane and methanol, saturated with ammonia, (97:3 by volume) as eluent. The pure fractions were collected and the eluent was evaporated. The residue was crystallized from acetonitrile. The product was filtered off and dried, yielding 2.5 parts (42,4%) of cis-4-amino-5-chloro-N-[1-[3-(1,3-dihydro-1,3-dioxo-2H-isoindol-2-yl)propyl]-3-methoxy-4-piperidinyl]-2-methoxybenzamide; mp. 208.2° C. (compound 88).

In a similar manner there was also prepared:
cis-4-amino-5-chloro-N-[1-[2-(1,3-dihydro-1,3-dioxo-2H-isoindol-2-yl)ethyl]-3-methoxy-4-piperidinyl]-2-methoxybenzamide hemihydrate; mp. 113.2° C. (compound 89).

Example 21

To a stirred suspension of 3.97 parts of cis-4-amino-5-chloro-2-methoxy-N-[3-methoxy-1-(4-oxopentyl)-4-piperidinyl]benzamide in 19.2 parts of ethanol was added first a solution of 0.72 parts of potassium cyanide in 12 parts of water and then 2.88 parts of ammonium carbonate. The whole was stirred overnight at about 55° C. After cooling, the reaction mixture was poured into water. Ethanol was evaporated whereupon a precipitate was formed. It was filtered off, washed with water and boiled twice in acetonitrile. The product was filtered off and crystallized from 4-methyl-2-pentanone, yielding 1.25 parts (26.7%) of cis-4-amino-5-chloro-2-methoxy-N-[3-methoxy-1-[3-(4-methyl-2,5-dioxo-4-imidazolidinyl)propyl]-4-piperidinyl]benzamide; mp. 235.8° C. (compound 90).

In a similar manner there was also prepared:
cis-4-amino-5-chloro-N-[1-[3-(2,5-dioxo-4-imidazolidinyl)propyl]-3-methoxy-4-piperidinyl]-2-methoxybenzamide; mp. 150.1° C. (compound 91).

Example 22

A mixture of 10 parts of 3,3-dimethyl-1,5-dioxaspiro[5.5]undecan-9-one, 9.42 parts of cis-4-amino-5-chloro-2-methoxy-N-(3-methoxy-4-piperidinyl)benzamide, 1 part of a solution of thiophene in methanol 4% and 200 parts of methanol was hydrogenated at normal pressure and at room temperature with 2 parts of platinum-on-charcoal catalyst 5%. After the calculated amount of hydrogen was taken up, the catalyst was filtered off and the filterate was evaporated. The residue was crystallized from acetonitrile. The product was filtered off and dried in vacuo at 60° C., yielding 9.33 parts (62.6%) of cis-4-amino-5-chloro-N-[1-(3,3-dimethyl-1,5-dioxaspiro[5.5]undec-9-yl)-3-methoxy-4-piperidinyl]-2-methoxybenzamide; mp. 187.5° C. (compound 92).

In a similar manner there were also prepared:
cis-4-amino-5-chloro-N-[1-[(1,4-dioxaspiro[4.5]dec-8-yl)methyl]-3-methoxy-4-piperidinyl]-2-methoxybenzamide; mp. 189.4° C. (compound 93);
ethyl trans-4-[4-[(4-amino-5-chloro-2-methoxybenzoyl)amino]-3-methoxy-1-piperidinyl]cyclohexanecarboxylate; mp. 153.0° C. (compound 94);
ethyl cis-4-[4-[(4-amino-5-chloro-2-methoxybenzoyl)amino]-3-methoxy-1-piperidinyl]cyclohexanecarboxylate; mp. 165.9° C. (compound 95);
(±)-[1(cis),3α,4α]-N-[1-(4-acetylcyclohexyl)-3-methoxy-4-piperidinyl]-4-amino-5-chloro-2-methoxybenzamide; mp. 205° C. (compound 96);
(±)-[1(trans),3α,4α]-N-[1-(4-acetylcyclohexyl)-3-methoxy-4-piperidinyl]-4-amino-5-chloro-2-methoxybenzamide; mp. 198.0° C. (compound 97);
(1,1-dimethylethyl) cis-[2-[4-[(4-amino-5-chloro-2-methoxybenzoyl)amino]-3-methoxy-1-piperidinyl]ethyl]methylcarbamate as a residue (compound 98);
(1,1-dimethylethyl) cis-[3-[4-[(4-amino-5-chloro-2-methoxybenzoyl)amino]-3-methoxy-1-piperidinyl]propyl]methylcarbamate; mp. 143.3° C. (compound 99); and
(1,1-dimethylethyl) cis-[4-[4-[(4-amino-5-chloro-2-methoxybenzoyl)amino]-3-methoxy-1-piperidinyl]butyl]methylcarbamate as a residue (compound 100).

Example 23

A mixture of 2.8 parts of cis-α-[[2-[4-[(4-amino-5-chloro-2-methoxybenzoyl)amino]-3-methoxy-1-piperidinyl]ethyl]aminocarbonyl]benzenemethanol acetate(ester), 1.1 parts of concentrated hydrochloric acid and 28 parts of methanol was stirred for 20 hours at reflux temperature. The reaction mixture was evaporated. The residue was taken up in water. The solution was treated with ammonia. The aqueous phase was extracted with dichloromethane. The organic layer was washed with water, dried, filtered and evaporated. The residue was crystallized from methanol. The product was filtered off and dried in vacuo at 50° C., yielding 0.67 parts (25.7%) of cis-N-[2-[4-[(4-amino-5-chloro-2-methoxybenzoyl)amino]-3-methoxy-1-piperidinyl]ethyl]-α-hydroxybenzeneacetamide; mp. 227.6° C. (compound 101).

Example 24

To a stirred solution of 2 parts of cis-4-amino-5-chloro-N-[3-hydroxy-1-[4-oxo-4-(1-pyrrolidinyl)butyl]-4-piperidinyl]-2-methoxybenzamide in 31.5 parts of tetrahydrofuran were added 0.7 parts of N,N-diethylethanamine. The whole was cooled in an ice bath and a solution of 0.72 parts of phenyl carbonochloridate in 13.5 parts of tetrahydrofuran was added dropwise to the thus obtained solution (slightly exothermic reaction). Upon complete addition, the whole was carbonochloridate in 9 parts of tetrahydrofuran was added. After stirring for 30 minutes in an ice bath, a solution of 0.07 parts of phenyl carbonochloridate in 9 parts of tetrahydrofuran was added. The whole was stirred further for 30 minutes in an ice bath and the reaction mixture was poured into water. The product was extracted with dichloromethane. The extract was dried, filtered and evaporated. The residue was crystallized from acetonitrile. After cooling to 0° C., the product was filtered off and dried in vacuo at 50° C., yielding 1.3 parts (50.5%) of cis-[4-[(4-amino-5-chloro-2-methoxybenzoyl)amino]-1-[4-oxo-4-(1-pyrrolidinyl)butyl]-3-piperidinyl]phenylcarbonate (compound 102).

In a similar manner there were also prepared:
cis-[4-[4-amino-5-chloro-2-methoxybenzoyl)amino]-1-[2-(3-ethyl-2-oxo-1-imidazolidinyl)ethyl]-3-piperdinyl]phenylcarbonate (compound 103); and
cis-[4-[4-amino-5-chloro-2-methoxybenzoyl)amino]-1-[2-[methyl(1-pyrrolidinylcarbonyl)amino]ethyl]-3-piperidinyl]phenylcarbonate (compound 104).

Example 25

To a stirred and cooled (ice/bath) solution of 3 parts of cis-[4-[4-amino-5-chloro-2-methoxybenzoyl)amino]-1-[2-(3-ethyl-2-oxo-1-imidazolidinyl)ethyl]-3-piperidinyl]phenylcarbonate in 135 parts of tetrahydrofuran was added a solution of 6.4 parts of pyrrolidine in 27 parts of tetrahydrofuran. Upon completion, stirring was continued for 1 hour at room temperature. The reaction mixture was poured into water. The product was extracted with dichloromethane. The extract was washed with water, dried, filtered and evaporated. The residue was boiled in 2,2'-oxybispropane and a few drops of acetonitrile. The product was filtered off and crystallized from acetonitrile at 0° C. It was filtered off again and dried in vacuo at 50° C., yielding 1.95 parts (66%) of cis-[4-[(4-amino-5-chloro-2-methoxybenzoyl)amino]-1-[2-(3-ethyl-2-oxo-1-imidazolidinyl)ethyl]-3-piperidinyl]-1-pyrrolidinecarboxylate; mp. 214.5° C. (compound 105).

In a similar manner there were also prepared:
cis-[4-[(4-amino-5-chloro-2-methoxybenzoyl)amino]-1-[4-oxo-4-(1-pyrrolidinyl)butyl]-3-piperidinyl]dimethylcarbamate; mp. 214.0° C. (compound 106);

cis-[4-[(4-amino-5-chloro-2-methoxybenzoyl)amino]-1-[2-(3-ethyl-2-oxo-1-imidazolidinyl)ethyl]-3-piperidinol]dimethylcarbamate; mp. 111.7° C. (compound 107); and cis-[4-[(4-amino-5-chloro-2-methoxybenzoyl)amino]-1-[2-[methyl(1-pyrrolidinylcarbonyl)amino]ethyl]-3-piperidinyl]dimethylcarbonate monohydrate; mp. 170.1° C. (compound 108).

Example 26

A mixture of 2.1 parts of cis-4-amino-5-chloro-N-[1-[4-(1,4-dioxa-8-azaspiro[4.5]dec-8-yl)-4-oxobutyl]-3-methoxy-4-piperidinyl]-2-methoxybenzamide, 0.74 parts of sulfuric acid and 40 parts of water was stirred for 2 hours at reflux temperature. After cooling, the reaction mixture was made alkaline with sodium carbonate while cooling. The product was extracted with trichloromethane. The extract was washed with water, dried, filtered and evaporated. The residue was crystallized from acetonitrile. The product was filtered off and dried in vacuo at 60° C., yielding 1 part (51.9%) cis-4-amino-5-chloro-2-methoxy-N-[3-methoxy-1-[4-oxo-4-(4-oxo-1-piperidinyl)butyl]-4-piperidinyl]benzamide; mp. 156.9° C. (compound 109).

In a similar manner there were also prepared:
cis-4-amino-5-chloro-2-methoxy-N-[3-methoxy-1-(4-oxocyclohexyl)-4-piperidinyl]benzamide; mp. 209.5° C. (compound 110);

cis-4-amino-5-chloro-2-methoxy-N-[3-methoxy-1-[(4-oxocyclohexyl)methyl]-4-piperidinyl]benzamide; mp. 211.6° C. (compound 111); and cis-N-[1-[4-(4-acetyl-1-piperidinyl)-4-oxobutyl]-3-methoxy-4-piperidinyl]-4-amino-5-chloro-2-methoxybenzamide; mp. 208.5° C. (compound 112).

Example 27

To a stirred and cooled (ice bath) solution of 3.30 parts of cis-4-amino-5-chloro-2-methoxy-N-[3-methoxy-1-[4-oxo-4-(1-pyrrolidinyl)butyl]-4-piperidinyl]benzamide in 225 parts of trichloromethane were added 1.55 parts of 3-chlorobenzenecarboperoxoic acid. The temperature was allowed to reach room temperature and the whole was stirred overnight. The mixture was concentrated. The concentrate was purified by column chromatography over silica gel using a mixture of trichloromethane and methanol, saturated with ammonia, (90:10 by volume) as eluent. The pure fractions were collected and the eluent was evaporated. The residue was taken up in acetonitrile and the whole was evaporated again. The crystallized product was filtered off and dried, yielding 2.45 parts (69.6%) of cis-4-amino-5-chloro-2-methoxy-N-[3-methoxy-1-[4-oxo-4-(1-pyrrolidinyl)butyl]-4-piperidinyl]benzamide,N-oxide; mp. 140.0° C. (compound 113).

Example 28

To a stirred solution of 4 parts of cis-4-amino-5-chloro-2-methoxy-N-[3-methoxy-1-[4-oxo-4-(1-pyrrolidinyl)butyl]-4-piperidinyl]benzamide in 20 parts of acetic acid were added 0,89 parts of acetic acid anhydride. Upon complete addition, stirring was continued overnight at room temperature. The reaction mixture was poured into water and the whole was treated with ammonium hydroxide while cooling. The product was extracted with dichloromethane. The extract was washed with water, dried, filtered and evaporated. The residue was solidified in a mixture of 2,2'-oxybispropane and a few drops of acetonitrile. The solid product was filtered off and crystallized from acetonitrile. After cooling to 0° C., the product was filtered off and dried in vacuo at 40° C., yielding 1.9 parts (42.8%) of cis-4-(acetylamino)-5-chloro-2-methoxy-N-[3-methoxy-1-[4-oxo-4-(1-pyrrolidinyl)butyl]-4-piperidinyl]benzamide hemihydrate; mp. 149.7° C. (compound 114).

C. Pharmacological Examples

The useful gastrointestestinal motility stimulating properties of the compounds of the present invention and their capability to accelerate the gastric emptying can be demonstrated in the following tests.

Example 29: Amplification of Contractions Induced by Submaximal Transmural Stimulation of the Guinea-Pig Ileum Non-terminal ileum segments of the guinea-pig were vertically suspended with a preload of 1 g in a 100 ml tyrode bath (37.5° C.) and gassed with a mixture of 95% $O_2$ and 5% $CO_2$. Contractions were measured isometrically. Transmural excitation was applied over the whole length of the ileum strip by means of two platinum electrodes (0.5 mm diameter), the anode was passed through the lumen of the ileum, the cathode was dipped in the bath solution. The tissue was excited with single rectangular stimuli of 1 msec duration and submaximal intensity at a frequency of 6 per minute, said stimuli being known to release acetylcholine from intramural nerve endings.

After a stabilization period of 30 minutes, a single dose of the test substance was added to the bath solution and its effect was followed for another 30 minutes. Drug effects were expressed as percentage of the initial contractility value before drug administration. Table 1 illustrates the lowest effective concentration of the test substance whereby a 20% increase was noted over the initial contractility before drug administration.

Reference: The Journal of Pharmacology and Experimental Therapeutics, 234, 775-783 (1985).

TABLE 1

| Comp. No. | Lowest effective concentration in mg/l |
|---|---|
| 80 | 0.00063 |
| 24 | 0.01 |
| 81 | 0.01 |
| 83 | 0.00063 |
| 101 | 0.01 |
| 23 | 0.01 |
| 48 | 0.00063 |
| 50 | 0.01 |
| 3 | 0.01 |
| 90 | 0.01 |
| 27 | 0.01 |
| 51 | 0.00063 |
| 52 | 0.01 |

TABLE 1-continued

| Comp. No. | Lowest effective concentration in mg/l |
|---|---|
| 53 | 0.00063 |
| 28 | 0.01 |
| 29 | 0.01 |
| 47 | 0.01 |
| 54 | 0.01 |
| 89 | 0.01 |
| 91 | 0.01 |
| 55 | 0.00063 |
| 56 | 0.01 |
| 109 | 0.01 |
| 57 | 0.01 |
| 4 | 0.01 |
| 61 | 0.00063 |
| 1 | 0.00063 |
| 59 | 0.01 |
| 112 | 0.01 |
| 6 | 0.00063 |
| 64 | 0.01 |
| 84 | 0.01 |
| 39 | 0.01 |
| 40 | 0.00063 |

Example 30: Amplification of Contractions Induced by Supramaximal Transmural Stimulation of the Guinea-Pig Ileum Non-terminal ileum segments of the guinea-pig were vertically suspended with a preload of 1 g in a 100 ml tyrode bath (37.5° C.) and gassed with a mixture of 95% $O_2$ and 5% $CO_2$. Contractions were measured isometrically. Transmural excitation was applied over the whole length of the ileum strip by means of two platinum electrodes (0.5 mm diameter), the anode was passed through the lumen of the ileum, the cathode was dipped in the bath solution. The tissue was excited with single rectangular stimuli of 1 msec duration and supramaximal intensity (maximal intensity +20 mA) at a frequency of 6 per minute. After a stabilization period of 30 minutes a single dose of the test compound was administered to the bath solution resulting in an end concentration of 0.01 mg/l. Five minutes later another dose was added to a total end concentration of 0.16 mg/ml. Drug effects were expressed as percentage of the initial contractility value before drug administration. Table 2 shows the percentage increase over the initial contractility at a concentration of 0.01 mg/l and 0.16 mg/l.

TABLE 2

| Comp. No. | Percentage increase over the initial contractility | |
|---|---|---|
| | dosage | |
| | 0.01 mg/l | 0.16 mg/l |
| 48 | 3.7 | 22.0 |
| 50 | 3.3 | 20.3 |
| 52 | 4.3 | 12.3 |
| 53 | 8.3 | 22.0 |
| 47 | 4.7 | 13.7 |
| 54 | 7.0 | 15.0 |
| 91 | 5.5 | 14.0 |
| 56 | 5.0 | 10.7 |
| 61 | 3.3 | 21.0 |
| 1 | 3.7 | 20.6 |
| 112 | 5.3 | 16.7 |
| 63 | 3.0 | 13.3 |
| 64 | 4.7 | 35.3 |

Example 31: Gastric Emptying of a Liquid Meal in Rats

Gastric emptying was measured in rats according to a modified version of a method originally devised by Reynell and Spray (J. Physiol.131:452–456, 1956). Rats were food deprived during 24 hours and isolated in individual cages. Water was withdrawn at the start of the experiments. The test meal, which consisted of a warm suspension of 200 mg phenol red in 40 ml distilled water was given by oral intubation (0.4 ml/rat) half an hour after subcutaneous administration of 0.16, 0.63, 2.5, 10 or 40 mg/kg of a compound of formula (I) or saline. The stomach was then exposed by laparotomy, quickly ligated at the pylorus and cardia, and removed. The stomach was cut up, and its contents was extracted with 100 ml of 0.1N sodium hydroxide. The phenol red content of this extract was assayed colorimetrically at 558 nm in a spectrophotometer. A mean value of 1.41 extinction units was obtained in saline-treated animals. Table 3 shows the mean extinction units following test injections of 0.16, 0.63, 2.5, 10 or 40 mg/kg test compound.

TABLE 3

| Comp. No. | Mean extinction units | | | | |
|---|---|---|---|---|---|
| | Dosage | | | | |
| | 0.16 mg/kg | 0.63 mg/kg | 2.5 mg/kg | 10 mg/kg | 40 mg/kg |
| 87 | 1.10 | 0.59 | 0.47 | 0.26 | 0.45 |
| 82 | 0.78 | 0.63 | 0.43 | 0.57 | — |
| 3 | 186 | 0.51 | 0.42 | 0.34 | — |
| 90 | 0.92 | 0.65 | 0.53 | 0.64 | 0.94 |
| 47 | 1.17 | 0.64 | 0.78 | 0.66 | — |
| 96 | 1.20 | 0.58 | 0.26 | 0.43 | — |
| 1 | 0.87 | 0.63 | 0.43 | 0.45 | 0.90 |
| 62 | — | 0.59 | 0.66 | 0.94 | 0.82 |
| 5 | 1.09 | 0.65 | 0.18 | 0.19 | 0.64 |
| 7 | 1.13 | — | 0.22 | 0.38 | 0.36 |
| 31 | 0.91 | — | 0.50 | 0.40 | 0.59 |
| 64 | 0.74 | 0.50 | 0.32 | 0.46 | — |
| 17 | 0.86 | 0.53 | 0.42 | 0.31 | 0.26 |
| 19 | 0.86 | 0.27 | 0.31 | 0.47 | 0.58 |
| 44 | 0.64 | 0.70 | 0.35 | 0.41 | 0.90 |
| 65 | 0.93 | 0.46 | 0.23 | 0.31 | — |

D) Composition Examples

The following formulations exemplify typical pharmaceutical compositions in dosage unit form suitable for systemic administration to animal and human subjects in accordance with the present invention. "Active ingredient" (A.I.) as used throughout these examples relates to a compound of formula (I), a N-oxide form, a pharmaceutically acceptable acid addition salt or a stereochemically isomeric form thereof.

Example 32: ORAL DROPS 500 g of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 0.01 g of the A.I. per ml. The resulting solution was filled into suitable containers.

Example 33: ORAL SOLUTION 9 g of methyl 4-hydroxybenzoate and 1 part of propyl 4-hydroxybenzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propanetriol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 0.005 g of the A.I. per teaspoonful (5 ml). The resulting solution was filled in suitable containers.

Example 34: CAPSULES 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 0.02 g of the A.I.

Example 35: FILM-COATED TABLETS

Preparation of Tablet Core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each comprising 0.01 g of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension (Opaspray K-1-2109 ®) and the whole was homogenated. The tablet cores were coated with the thus obtained mixture in a coating apparatus.

Example 36: INJECTABLE SOLUTION 1.8 g methyl 4-hydroxybenzoate and 0.2 propyl 4-hydroxybenzoate were dissolved in about 0.5 l of boiling water for injection. After cooling to about 50° C. there were added while stirring 4 g lactic acid, 0.05 propylene glycol and 4 g of the A.I. The solution was cooled to room temperature and supplemented with water for injection q.s. ad 1 l volume, giving a solution of 0.004 g A.I. per ml. The solution was sterilized by filtration (U.S.P. XVII p. 811) and filled in sterile containers.

Example 37 : SUPPOSITORIES 3 g A.I. was dissolved in a solution of 3 g 2,3-dihydroxybutanedioic acid in 25 ml polyethylene glycol 400. 12 G surfactant (SPAN ®) and triglycerides (Witepsol 555 ®) q.s. ad 300 g were molten together. The latter mixture was mixed well with the former solution. The thus obtained mixture was poured into moulds at a temperature of 37°~38° C. to form 100 suppositories each containing 0/03 g of the active ingredient.

We claim:

1. A compound of the formula:

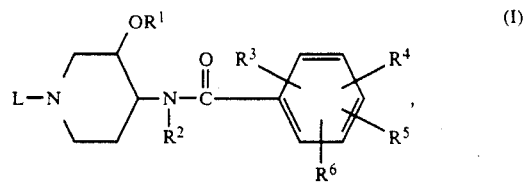

an N-oxide form, a pharmaceutically acceptable acid addition salt, or a stereoisomeric form thereof, wherein:

$R^1$ represents hydrogen, $C_{1-6}$alkyl, aryl$C_{1-6}$alkyl, $C_{1-6}$alkylcarbonyl, $C_{1-6}$alkoxycarbonyl, aryloxycarbonyl, amino$C_{1-6}$alkyl, mono- or di($C_{1-6}$alkyl)amino$C_{1-6}$alkyl, aminocarbonyl, mono- or di($C_{1-6}$alkyl)aminocarbonyl, pyrrolidinylcarbonyl, or piperidinylcarbonyl;

wherein aryl represents phenyl optionally substituted with 1, 2, or 3 substituents each independently selected from halo, hydroxy, $C_{1-6}$alkyl, $C_{1-6}$alkyloxy, aminosulfonyl, $C_{1-6}$alkylcarbonyl, nitro, trifluoromethyl, amino, aminocarbonyl, and phenylcarbonyl;

$R^2$ represents hydrogen or $C_{1-6}$alkyl;

$R^3$, $R^4$, and $R^5$ each independently represent hydrogen, $C_{1-6}$alkyl, $C_{1-6}$alkyloxy, halo, hydroxy, cyano, nitro, amino, trifluoromethyl, mono- or di($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylaminosulfonyl, $C_{1-6}$alkylsulfinyl, $C_{1-6}$alkylsulfonyl, $C_{1-6}$alkylthio, mercapto, aryl$C_{1-6}$alkyloxy, or aryloxy, wherein aryl is as defined above;

$R^6$ represents hydrogen, hydroxy, $C_{1-6}$alkyl, $C_{1-6}$alkyloxy, halo, or amino; and L represents a radical of the formula:

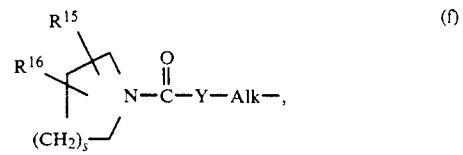

(f)

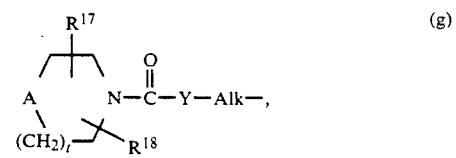

(g)

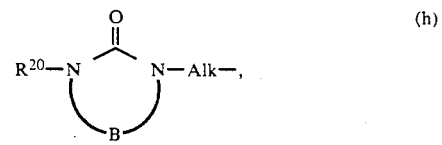

(h)

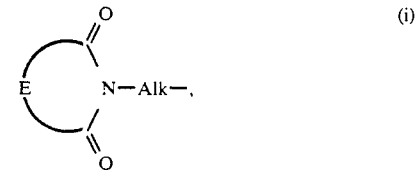

(i)

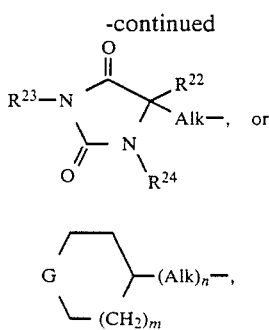

(j)

(k)

wherein:

Y represents O, S, $NR^7$, or a direct bond, wherein $R^7$ represents hydrogen or $C_{1-6}$alkyl;

$R^{15}$ and $R^{16}$ each independently represent hydrogen, $C_{1-6}$alkyl, hydroxy, $C_{1-6}$alkyloxy, amino, mono- or di($C_{1-6}$alkyl)amino, hydroxy$C_{1-6}$alkyl, $C_{1-6}$alkylcarbonyl, $C_{1-6}$alkyloxycarbonyl, aminocarbonyl, mono- or di($C_{1-6}$alkyl)-aminocarbonyl, or 2-$C_{1-6}$alkyl-1,3-dioxolan-2-yl, or $R^{15}$ and $R^{16}$ combined with the carbon atom bearing said $R^{15}$ and $R^{16}$ may form a carbonyl or a 1,3-dioxolan-2-ylidene radical;

s represents 1, 2, or 3;

A represents O, S, or $NR^{19}$, wherein said $R^{19}$ represents hydrogen, $C_{1-6}$alkyl, aryl, pyridinyl, pyrimidinyl, $C_{1-6}$alkylcarbonyl, $C_{1-6}$alkyloxycarbonyl, or aryl$C_{1-6}$alkyl, wherein aryl is as defined above;

$R^{17}$ and $R^{18}$ each independently represent hydrogen or $C_{1-6}$alkyl, or when A represents $NR^{19}$, $R^{17}$ and $R^{18}$ taken together may form a fused benzene residue being optionally substituted with halo or $C_{1-6}$alkyl;

t represents the integer 1 or 2;

$R^{20}$ represents hydrogen or $C_{1-6}$alkyl;

B represents a bivalent radical of the formula —CH$_2$—CH$_2$—, -C(=O)—CH$_2$—, or —CH$_2$—CH$_2$—CH$_2$—, wherein each hydrogen atom independently may be replaced by $C_{1-6}$alkyl substituents, or when $R^{20}$ represents $C_{1-6}$alkyl, said bivalent radical may also be 1,2-benzenediyl optionally substituted with halo or $C_{1-6}$alkyl;

E represents a bivalent radical of the formula —CH$_2$—CH$_2$—, —CH$_2$—N($R^{21}$)—, or —CH$_2$—CH$_2$—CH$_2$—, wherein each hydrogen atom independently may be replaced by $C_{1-6}$alkyl, or said bivalent radical may also be 1,2-benzenediyl optionally substituted with halo or $C_{1-6}$alkyl, wherein said $R^{21}$ represents hydrogen or $C_{1-6}$alkyl;

$R^{22}$, $R^{23}$, and $R^{24}$ each independently represent hydrogen or $C_{1-6}$alkyl;

n and m each independently represent 0 or 1; and

G represents carbonyl, carboxymethylene, $C_{1-6}$alkyloxycarbonylmethylene, $C_{1-6}$alkylcarbonylmethylene, 5,5-dimethyl-1,3-dioxan-2-ylidene or, 1,3-dioxolan-2ylidene.

2. A compound according to claim 1 wherein $R^1$ is hydrogen, $C_{1-6}$alkyl, aryloxycarbonyl, mono- or di($C_{1-6}$alkyl)aminocarbonyl, pyrrolidinylcarbonyl or piperidinylcarbonyl; $R^2$ is hydrogen; and $R^3$, $R^4$ and $R^5$ each independently are hydrogen, halo, $C_{1-6}$alkyloxy, amino, mono- or di($C_{1-6}$alkyl)amino, $C_{1-6}$alkylcarbonylamino, nitro, aminosulfonyl, $C_{1-6}$alkylaminosulfonyl or $C_{1-6}$alkylsulfonyl.

3. A compound according to claim 2 wherein the substituents on the 3- and the 4position of the piperidine ring have the cis configuration.

4. A compound according to claim 3 wherein aryl represents phenyl optionally substituted with 1, 2, or 3 substituents each independently selected from halo, hydroxy, $C_{1-4}$alkyl, and $C_{1-4}$alkyloxy, Alk represents a $C_{1-4}$alkanediyl group, and L represents a group of the formula:

(f) wherein Y represents O, $NR^7$, or a direct bond, $R^{15}$ represents hydrogen, $C_{1-4}$alkyl, hydroxy, $C_{1-4}$alkyloxy, amino, mono- or di($C_{1-4}$alkyl)amino, hydroxy$C_{1-4}$alkyl, $C_{1-4}$alkylcarbonyl, $C_{1-4}$alkyloxycarbonyl, or aminocarbonyl, and $R^{16}$ represents hydrogen or $C_{1-4}$alkyl, or $R^{15}$ and $R^{16}$ combined with the carbon atom bearing said $R^{15}$ and $R^{16}$ may form a carbonyl or a 1,3-dioxolan-2-ylidene radical; or (g) wherein Y represents O, $NR^7$, or a direct bond and A represents O or $NR^{19}$, wherein $R^{19}$ represents hydrogen, $C_{1-6}$alkyl, aryl, pyridinyl, pyrimidinyl, $C_{1-4}$alkylcarbonyl, $C_{1-4}$alkyloxycarbonyl, or aryl$C_{1-4}$alkyl; or (h) wherein B represents 1,2-ethanediyl or when $R^{20}$ represents $C_{1-4}$alkyl B may also be 1,2-benzenediyl optionally substituted with halo or $C_{1-4}$alkyl; or (i) wherein E represents 1,3-propanediyl optionally substituted with $C_{1-4}$alkyl, 1,2-benzenediyl optionally substituted with halo or $C_{1-4}$alkyl, or a bivalent radical of the formula —CH$_2$—N($R^{21}$)—, said $R^{21}$ being hydrogen or $C_{1-4}$alkyl; or (j) wherein $R^{23}$ and $R^{24}$ are both hydrogen; or (k) wherein G represents carbonyl, $C_{1-4}$alkyloxycarbonylmethylene, $C_{1-4}$alkylcarbonylmethylene, 5,5-dimethyl-1,3-dioxan-2-ylidene, or 1,3-dioxolan-2-ylidene.

5. A compound according to claim 4 wherein the benzamide part is substituted on the meta position with $R^3$ being chloro, bromo, $C_{1-4}$alkylaminosulfonyl, aminosulfonyl or $C_{1-4}$alkylsulfonyl, on the para position with $R^4$ being amino and on the ortho position with $R^5$ being hydroxy or $C_{1-4}$alkyloxy.

6. A compound according to claim 1 wherein L is a radical of formula (k).

7. A compound according to claim 1 wherein L is a radical of formula (f), (g), (h) or (i).

8. The compound of claim 1 wherein said compound is a cis-4-amino-5-chloro-2-methoxy-N[3-methoxy-1-alkyl-4-piperidinyl]-benzamide.

9. The compound of claim 8 wherein said compound is a member selected from the group consisting of:
cis-4-amino-5-chloro-2-methoxy-N-[3-methoxy-[4-oxo-4-(1-pyrrolidinyl)butyl]-4piperidinyl]benzamide;
cis-4-amino-5-chloro-2-methoxy-N-[3-methoxy-[4-oxo-4(1-piperidinyl)butyl]-4-piperidinyl]benzamide;
cis-4-amino-5-chloro-2-methoxy-N-[3-methoxy-[3-methyl-4-oxo-4-(1-piperidinyl)butyl]-4-piperidinyl]-benzamide;
cis-4-amino-5-chloro-N-[1-[2-(3-ethyl-2-oxo-1-imidazolinyl)-ethyl]-3-methoxy-4-piperidinyl]-2-methoxybenzamide;
cis-4-amino-5-chloro-2-methoxy-N-[3-methoxy-1-[4-oxo-4-(2-oxo-1-pyrrolidinyl)butyl]-4-piperidinyl]benzamide;
cis-4-amino-5-chloro-2-methoxy-N-[3-methoxy-1-[3-methyl-4-(2-methyl-1-piperidinyl)-4-oxobutyl]-4-piperidinyl]benzamide; and cis-4-amino-5-chloro-N-[1-[4-[4-(dimethylamino)-1-piperidinyl]-4-oxobutyl]-3-methoxy-4-piperidinyl]-2-methoxybenzamide.

10. A pharmaceutical composition comprising one or more inert carriers and as active ingredient a gastrointestinal motility stimulating amount of a compound as claimed in claim 1.

11. A pharmaceutical composition according to claim 10 wherein $R^1$ is hydrogen, $C_{1-6}$alkyl, aryloxycarbonyl, mono- or di($C_{1-6}$alkyl)aminocarbonyl, pyrrolidinylcarbonyl or piperidinylcarbonyl; $R^2$ is hydrogen; and $R^3$, $R^4$ and $R^5$ each independently are hydrogen, halo, $C_{1-6}$alkyloxy, amino, mono- or di($C_{1-6}$alkyl)amino, $C_{1-6}$alkylcarbonylamino, nitro, aminosulfonyl, $C_{1-6}$alkylaminosulfonyl or $C_{1-6}$alkylsulfonyl.

12. A pharmaceutical composition according to claim 11 wherein the substituents on the 3- and the 4- position of the piperidine ring have the cis configuration.

13. A pharmaceutical composition according to claim 12 wherein aryl represents phenyl optionally substituted with 1, 2, or 3 substituents each independently selected from halo, hydroxy, $C_{1-4}$alkyl, and $C_{1-4}$alkyloxy, Alk represents a $C_{1-4}$alkanediyl group, and L represents a group of the formula:
  (f) wherein Y represents O, $NR^7$, or a direct bond, $R^{15}$ represents hydrogen, $C_{1-4}$alkyl, hydroxy, $C_{1-4}$alkyloxy, amino, mono- or di($C_{1-4}$alkyl)amino, hydroxy$C_{1-4}$alkyl, $C_{1-4}$alkylcarbonyl, $C_{1-4}$alkyloxycarbonyl, or aminocarbonyl, and $R^{16}$ represents hydrogen or $C_{1-4}$alkyl, or $R^{15}$ and $R^{16}$ combined with the carbon atom bearing said $R^{15}$ and $R^{16}$ may form a carbonyl or a 1,3-dioxolan-2-ylidene radical; or
  (g) wherein Y represents O, $NR^7$, or a direct bond and A represents O or $NR^{19}$, wherein $R^{19}$ represents hydrogen, $C_{1-6}$alkyl, aryl, pyridinyl, pyrimidinyl, $C_{1-4}$alkylcarbonyl, $C_{1-4}$alkyloxycarbonyl, or aryl$C_{1-4}$alkyl; or
  (h) wherein B represents 1,2-ethanediyl or when $R^{20}$ represents $C_{1-4}$alkyl B may also be 1,2-benzenediyl optionally substituted with halo or $C_{1-4}$alkyl; or
  (i) wherein E represents 1,3-propanediyl optionally substituted with $C_{1-4}$alkyl, 1,2-benzenediyl optionally substituted with halo or $C_{1-4}$alkyl, or a bivalent radical of the formula —$CH_2$—$N(R^{21})$—, said $R^{21}$ being hydrogen or $C_{1-4}$alkyl; or
  (j) wherein $R^{23}$ and $R^{24}$ are both hydrogen; or
  (k) wherein G represents carbonyl, $C_{1-4}$alkyloxycarbonylmethylene, $C_{1-4}$alkylcarbonylmethylene, 5,5-dimethyl-1,3-dioxan-2-ylidene, or 1,3-dioxolan-2-ylidene.

14. A pharmaceutical composition according to claim 13 wherein the benzamide part is substituted on the meta position with $R^3$ being chloro, bromo, $C_{1-4}$alkylaminosulfonyl, aminosulfonyl or $C_{1-4}$alkylsulfonyl, on the para position with $R^4$ being amino and on the ortho position with $R^5$ being hydroxy or $C_{1-4}$alkyloxy.

15. A pharmaceutical composition according to claim 10 wherein L is a radical of formula (f), (g), (h) or (i).

16. A method of treating warm-blooded animals suffering from motility disorders of the gastrointestinal system, which method comprises the systemic administration to said warm-blooded animals of an effective gastrointestinal stimulating amount of a compound as claimed in claim 1.

17. A method according to claim 16 wherein $R^1$ is hydrogen, $C_{1-6}$alkyl, aryloxycarbonyl, mono- or di($C_{1-6}$alkyl)aminocarbonyl, pyrrolidinylcarbonyl or piperidinylcarbonyl; $R^2$ is hydrogen; and $R^3$, $R^4$ and $R^5$ each independently are hydrogen, halo, $C_{1-6}$alkyloxy, amino, mono- or di($C_{1-6}$alkyl)amino, $C_{1-6}$alkylcarbonylamino, nitro, aminosulfonyl, $C_{1-6}$alkylaminosulfonyl or $C_{1-6}$alkylsulfonyl.

18. A method according to claim 17 wherein the substituents on the 3- and the 4- position of the piperidine ring have the cis configuration.

19. A method according to claim 18 wherein aryl represents phenyl optionally substituted with 1, 2, or 3 substituents each independently selected from halo, hydroxy, $C_{1-4}$alkyl, and $C_{1-4}$alkyloxy, Alk represents a $C_{1-4}$alkanediyl group, and L represents a group of the formula:
  (f) wherein Y represents O, $NR^7$, or a direct bond, $R^{15}$ represents hydrogen, $C_{1-4}$alkyl, hydroxy, $C_{1-4}$alkyloxy, amino, mono- or di($C_{1-4}$alkyl)amino, hydroxy$C_{1-4}$alkyl, $C_{1-4}$alkylcarbonyl, $C_{1-4}$alkyloxycarbonyl, or aminocarbonyl, and $R^{16}$ represents hydrogen or $C_{1-4}$alkyl, or $R^{15}$ and $R^{16}$ combined with the carbon atom bearing said $R^{15}$ and $R^{16}$ may form a carbonyl or a 1,3-dioxolan-2-ylidene radical; or
  (g) wherein Y represents O, $NR^7$, or a direct bond and A represents O or $NR^{19}$, wherein $R^{19}$ represents hydrogen, $C_{1-6}$alkyl, aryl, pyridinyl, pyrimidinyl, $C_{1-4}$alkylcarbonyl, $C_{1-4}$alkyloxycarbonyl, or aryl$C_{1-4}$alkyl; or
  (h) wherein B represents 1,2-ethanediyl or when $R^{20}$ represents $C_{1-4}$alkyl B may also be 1,2-benzenediyl optionally substituted with halo or $C_{1-4}$alkyl; or
  (i) wherein E represents 1,3-propanediyl optionally substituted with $C_{1-4}$alkyl, 1,2-benzenediyl optionally substituted with halo or $C_{1-4}$alkyl, or a bivalent radical of the formula —$CH_2$—$N(R^{21})$—, said $R^{21}$ being hydrogen or $C_{1-4}$alkyl; or
  (j) wherein $R^{23}$ and $R^{24}$ are both hydrogen; or
  (k) wherein G represents carbonyl, $C_{1-4}$alkyloxycarbonylmethylene, $C_{1-4}$alkylcarbonylmethylene, 5,5-dimethyl-1,3-dioxan-2-ylidene, or 1,3-dioxolan-2-ylidene.

20. A method according to claim 19 wherein the benzamide part is substituted on the meta position with $R^3$ being chloro, bromo, $C_{1-4}$alkylaminosulfonyl, aminosulfonyl or $C_{1-4}$alkylsulfonyl, on the para position with $R^4$ being amino and on the ortho position with $R^5$ being hydroxy or $C_{1-4}$alkyloxy.

21. A method according to claim 16 wherein L is a radical of formula (f), (g), (h) or (i).

22. The pharmaceutical composition according to claim 10 wherein said compound is a cis-4-amino-5-chloro-2-methoxy-N-[3-methoxy-1-alkyl-4-piperidinyl]-benzamide.

23. The pharmaceutical composition according to claim 22 wherein said compound is a member selected from the group consisting of:
cis-4-amino-5-chloro-2-methoxy-N-[3-methoxy-[4-oxo-4-(1-pyrrolidinyl)butyl]-4piperidinyl]benzamide;
cis-4-amino-5-chloro-2-methoxy-N-[3-methoxy-[4-oxo-4-(1-piperidinyl)butyl]-4-piperidinyl]benzamide;
cis-4-amino-5-chloro-2-methoxy-N-[3-methoxy-[3-methyl-4-oxo-4-(1-piperidinyl)butyl]-4-piperidinyl]-benzamide;
cis-4-amino-5-chloro-N-[1-[2-(3-ethyl-2oxo-1-imidazolinyl)-ethyl]-3-methoxy-4piperidinyl]-2-methoxybenzamide;

cis-4-amino-5-chloro-2-methoxy-N-[3-methoxy-1-[4-oxo-4-(2-oxo-1-pyrrolidinyl)butyl]-4-piperidinyl]benzamide;

cis-4-amino-5-chloro-2-methoxy-N-[3-methoxy-1-[3-methyl-4-(2-methyl-1-piperidinyl)-4-oxobutyl]-4-piperidinyl]benzamide; and cis-4-amino-5-chloro-N-[1-[4-[4-(dimethylamino)-1-piperidinyl]-4-oxobutyl]-3-methoxy-4-piperidinyl]-2-methoxybenzamide.

24. The method according to claim 16 wherein said compound is a cis-4-amino-5-chloro-2-methoxy-N-[3-methoxy-1-alkyl-4-piperidinyl]benzamide.

25. The method according to claim 24 wherein said compound is a member selected from the group consisting of:

cis-4-amino-5-chloro-2-methoxy-N-[3-methoxy-[4-oxo-4-(1-pyrrolidinyl)butyl]-4-piperidinyl]benzamide;

cis-4-amino-5-chloro-2-methoxy-N-[3-methoxy-[4-oxo-4-(1-piperidinyl)butyl]-4-piperidinyl]benzamide;

cis-4-amino-5-chloro-2-methoxy-N-[3-methoxy-[3-methyl-4-oxo-4-(1-piperidinyl)butyl]-4-piperidinyl]benzamide;

cis-4-amino-5-chloro-N-[1-[2-(3-ethyl-2-oxo-1-imidazolinyl)-ethyl]-3-methoxy-4-piperidinyl]-2-methoxybenzamide;

cis-4-amino-5-chloro-2-methoxy-N-[3-methoxy-1-[4-oxo-4-(2-oxo-1-pyrrolidinyl)butyl]-4-piperidinyl]benzamide;

cis-4-amino-5-chloro-2-methoxy-N-[3-methoxy-1-[3-methyl-4-(2-methyl-1-piperidinyl)-4-oxobutyl]-4-piperidinyl]benzamide; and cis-4-amino-5-chloro-N-[1-[4-[4-(dimethylamino)-1-piperidinyl]-4-oxobutyl]-3-methoxy-4-piperidinyl]-2-methoxybenzamide.

* * * * *